(12) United States Patent
Savoie

(10) Patent No.: US 12,144,762 B2
(45) Date of Patent: Nov. 19, 2024

(54) DEVICE FOR SANITARILY DRAINING HUMAN WASTE FROM AN OSTOMY POUCH INTO A TOILET

(71) Applicant: Hugh Joseph Savoie, Bonny River (CA)

(72) Inventor: Hugh Joseph Savoie, Bonny River (CA)

( * ) Notice: Subject to any disclaimer, the term of this patent is extended or adjusted under 35 U.S.C. 154(b) by 271 days.

(21) Appl. No.: 17/691,959

(22) Filed: Mar. 10, 2022

(65) Prior Publication Data

US 2023/0285179 A1    Sep. 14, 2023

(51) Int. Cl.
| | |
|---|---|
| *A61F 5/445* | (2006.01) |
| *A61F 5/44* | (2006.01) |
| *B65B 69/00* | (2006.01) |
| *E03D 11/02* | (2006.01) |
| *E03D 13/00* | (2006.01) |
| *B67C 11/00* | (2006.01) |

(52) U.S. Cl.
CPC ............ *A61F 5/445* (2013.01); *A61F 5/4405* (2013.01); *B65B 69/00* (2013.01); *E03D 11/02* (2013.01); *E03D 13/00* (2013.01); *B67C 11/00* (2013.01)

(58) Field of Classification Search
CPC .............................. B65B 69/0016; A61F 5/445
See application file for complete search history.

(56) References Cited

U.S. PATENT DOCUMENTS

| | | | |
|---|---|---|---|
| 2,568,857 A | 9/1951 | Jacobs | |
| 2,664,573 A * | 1/1954 | Inez ......................... | A61F 5/445 4/661 |
| 2,864,094 A * | 12/1958 | Williams, Jr. ........... | A61G 9/00 D24/123 |
| 4,282,611 A * | 8/1981 | O'Day .................. | E03D 11/025 4/144.1 |
| 4,285,076 A | 8/1981 | Dickstein | |
| 6,224,581 B1 * | 5/2001 | Withers .................. | A61F 5/445 604/332 |
| 6,546,566 B1 | 4/2003 | Geisel | |
| 6,848,126 B2 * | 2/2005 | Marcellus ................ | A47K 4/00 4/321 |

(Continued)

FOREIGN PATENT DOCUMENTS

| | | | |
|---|---|---|---|
| CA | 3099012 C | | 3/2024 |
| JP | 2004188156 | * | 7/2004 |

(Continued)

*Primary Examiner* — J C Jacyna
(74) *Attorney, Agent, or Firm* — Inventech Patent Services, LLC; Marc A. Scharich

(57) ABSTRACT

A device for sanitarily draining human waste from an ostomy pouch into a toilet includes a base, a main support coupled to the base, a holder coupled to the main support, and a basin retained by the holder. The basin has a top end having a top lip forming a top opening and a bottom end having a bottom opening formed therein. The top lip of the basin is supported by the holder such that at least the weight of the basin is applied to the holder by way of at least the top lip. A drain is coupled to the basin at the bottom opening and is in fluid communication with the basin. The basin is capable of receiving therein human waste drained from an ostomy pouch. The drain is capable of at least directing and draining any human waste received from the basin into a toilet.

21 Claims, 20 Drawing Sheets

(56) References Cited

U.S. PATENT DOCUMENTS

| | | | |
|---|---|---|---|
| 8,424,125 B2* | 4/2013 | Anderson | E03D 11/025 |
| | | | 4/144.1 |
| 8,640,270 B1 | 2/2014 | Garofano | |
| 9,492,308 B2 | 11/2016 | Plath | |
| 9,605,420 B1 | 3/2017 | Berger | |
| 9,637,906 B1 | 5/2017 | Charles | |
| 9,863,130 B1 | 1/2018 | Abram | |
| 10,865,555 B2 | 12/2020 | Abrahams | |
| 11,639,244 B2 | 5/2023 | Foda et al. | |
| 2021/0070488 A1 | 3/2021 | Foda | |

FOREIGN PATENT DOCUMENTS

| | | | |
|---|---|---|---|
| KR | 100840073 B1 | 6/2008 | |
| WO | 2019213762 A1 | 11/2019 | |

* cited by examiner

DEVICE FOR SANITARILY DRAINING HUMAN WASTE FROM AN OSTOMY POUCH INTO A TOILET

TECHNICAL FIELD

The present disclosure relates generally to ostomy pouch care and, more particularly, to a device for sanitarily draining human waste from an ostomy pouch into a toilet.

BACKGROUND

This section provides background information related to the present disclosure which is not necessarily prior art.

An ostomy is a type of surgical procedure pertaining to intestinal or urinary diversion. Various types of ostomies may include a colostomy (i.e., a diversion of a colon to an abdominal wall surface), an ileostomy (i.e., a diversion of a terminal end of a small intestine, the ileum, to an abdominal wall surface), and a urostomy (i.e., a urinary diversion of an isolated segment of the ileum to an abdominal wall surface). Such aforementioned ostomies are typically performed on people suffering from cancers, traumatic injuries, inflammatory bowel diseases, and other intestinal or urinary tract abnormalities.

After the completion of an ostomy, a person is typically left with a surgically-crafted abdominal wall opening (i.e., a stoma) that allows human waste (e.g., feces, urine, etc.) to flow out of the person's body. Depending on a person's particular health-related condition, the stoma may be temporary (i.e., being surgically reversed after a period of time) or may be permanent. As such, after the completion of an ostomy, a person typically needs to employ an ostomy pouch that is removably securable to the person's abdomen around the stoma for the collection and temporary storage of human waste.

An ostomy pouch is typically drainable, washable, and reusable, and as such, typically needs periodic draining when it is approximately one-third to one-half full of human waste. In this regard, once an ostomy pouch needs draining, the human waste collected in the ostomy pouch is often freely drained directly into a toilet. While attempting to freely drain human waste from an ostomy pouch directly into a toilet, a person may need to stand over the toilet, sit on the toilet, straddle the toilet, or kneel on the floor next to the toilet. Unfortunately, freely draining human waste from an ostomy pouch directly into a toilet from such aforementioned positions often results in excessive human waste soiling and splashing the person and the surrounding area in and around the toilet (i.e., due to the physical space or gap between the ostomy pouch, which typically remains secured to the person's abdomen, and the waterline within the toilet). In this regard, the person may therefore experience physical discomfort or anxiety while freely draining human waste from the ostomy pouch directly into the toilet.

In an attempt to make ostomy pouch care more convenient, various waste-collection devices (i.e., for the collecting and/or draining of human waste) have been developed. Some existing waste-collection devices aim to assist in draining human waste from a stoma or an ostomy pouch into a toilet, such as while a person is either sitting or standing. Unfortunately, these existing waste-collection devices often present various challenges and limitations. For example, many existing waste-collection devices are typically bulky and lack sufficient portability or adjustability, thus leading to various difficulties when handling, moving, or using the waste-collection devices. This is especially problematic since many toilets in bathrooms or restrooms are located within relatively tight spaces (e.g., next to or between walls, vanities, tubs, showers, etc.). Additionally, many existing waste-collection devices have relatively small or narrow openings through which human waste may be received when drained from an ostomy pouch, thus causing more difficulty, inconvenience, and potential problems when draining the ostomy pouch. Additionally, many existing waste-collection devices are not easily washable, and thus may not be able to be properly or easily sanitized after use. Additionally, most existing waste-collection devices typically do not include sufficient accessories or features that provide additional conveniences while using the waste-collection devices. In this regard, for example, most existing waste-collection devices typically do not allow for an ostomy pouch to be properly washed or sanitized at the location of the waste-collection device, thus forcing a person to wash or sanitize the ostomy pouch at a different location after draining the ostomy pouch.

Therefore, there is a continuing unaddressed need for a device that may be used for sanitarily draining human waste from an ostomy pouch into a toilet, and that is capable of overcoming at least the aforementioned challenges and limitations associated with the aforementioned existing waste-collection devices.

SUMMARY

At least the above-identified unaddressed need is addressed with the present disclosure.

This section provides a general summary of the present disclosure and is not a comprehensive disclosure of its full scope or all of its features.

In one or more illustrative embodiments of the present disclosure, a device for sanitarily draining human waste from an ostomy pouch into a toilet includes a base, a main support coupled to the base, a holder coupled to the main support, and a basin retained by the holder. The basin has a top end having a top lip forming a top opening and a bottom end having a bottom opening formed therein. The top lip of the basin is supported by the holder such that at least the weight of the basin is applied to the holder by way of at least the top lip. The device further includes a drain coupled to the basin at the bottom opening of the basin such that the drain is in fluid communication with the basin. The basin is capable of receiving therein human waste drained from an ostomy pouch. The drain is capable of at least directing and draining any human waste received from the basin into a toilet.

In one or more illustrative embodiments of the present disclosure, a device for sanitarily draining human waste from an ostomy pouch into a toilet includes a base, a main support coupled to the base, a holder coupled to the main support, and a basin retained by the holder. The basin has an upper portion, a lower portion, and an intermediate portion disposed between the upper and lower portions. The upper portion of the basin has a top end having a top opening formed therein. The lower portion of the basin has a bottom end having a bottom opening formed therein. The basin is at least partially surrounded by the holder at a location above the lower portion of the basin. The device further includes a drain coupled to the basin at the bottom opening of the basin such that the drain is in fluid communication with the basin. The basin is capable of being lifted and removed from the holder while the holder is coupled to the main support. The basin is further capable of receiving therein human waste drained from an ostomy pouch. The drain is capable of at least directing and draining any human waste received from the basin into a toilet.

In one or more illustrative embodiments of the present disclosure, a device for sanitarily draining human waste from an ostomy pouch into a toilet includes a base and a main support coupled to the base and extending upwardly from the base. The main support has a vertically-extending center axis. The device further includes a basin operably coupled to the main support. The basin has a top end having a top annular edge forming a top opening, a bottom end having a bottom opening formed therein, a generally concave inner surface extending from the top end to the bottom end and entirely around the basin, and a generally convex outer surface extending from the top end to the bottom end and entirely around the basin. The basin further has a vertically-extending center axis. The vertically-extending center axis of the basin is laterally offset from the vertically-extending center axis of the main support. The device further includes a drain coupled to the basin at the bottom opening of the basin such that the drain is in fluid communication with the basin. The basin is capable of receiving therein human waste drained from an ostomy pouch. The drain is capable of at least directing and draining any human waste received from the basin into a toilet.

In one or more illustrative embodiments of the present disclosure, a device for sanitarily draining human waste from an ostomy pouch into a toilet includes a base. The base includes a stationary portion capable of being mounted on a toilet rearward of a toilet bowl opening of the toilet and forward of a tank of the toilet, and an arm portion pivotally coupled to the stationary portion and extending laterally outwardly from the stationary portion. The device further includes a main support coupled to the arm portion of the base and extending upwardly from the arm portion. The device further includes a holder coupled to the main support. The device further includes a basin operably coupled to the main support by way of at least a portion of the holder. The basin has a top end having a top opening formed therein and a bottom end having a bottom opening formed therein. The device further includes a drain coupled to the basin at the bottom opening of the basin such that the drain is in fluid communication with the basin. The basin is capable of receiving therein human waste drained from an ostomy pouch. The drain is capable of at least directing and draining any human waste received from the basin into the toilet.

BRIEF DESCRIPTION OF THE DRAWINGS

The present disclosure will become more fully understood from the detailed description and the accompanying drawings, wherein.

DETAILED DESCRIPTION

As required, one or more detailed embodiments of the present disclosure are disclosed herein, however, it is to be understood that the disclosed embodiments are merely illustrative of the present disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure. Furthermore, the use of a singular term, such as, "a" is not to be interpreted as limiting the number of components or details of particular components. Additionally, various terms and/or phrases describing or indicating a position or directional reference such as, but not limited to, "top", "bottom", "front", "rear", "forward", "rearward", "end", "outer", "inner", "left", "right", "vertical", "horizontal", "upper", "lower", etc. may relate to one or more particular components as seen generally from a user's vantage point during use or operation, and such terms and/or phrases are not to be interpreted as limiting, but merely as a representative basis for describing the present disclosure to one skilled in the art.

Referring to FIGS. 1-7, 20 and 21, one illustrative embodiment of a device 10 for sanitarily draining human waste (e.g., feces, urine, etc.) 406 from an ostomy pouch 500 into a toilet 600 will now be described in detail.

Figure 3:
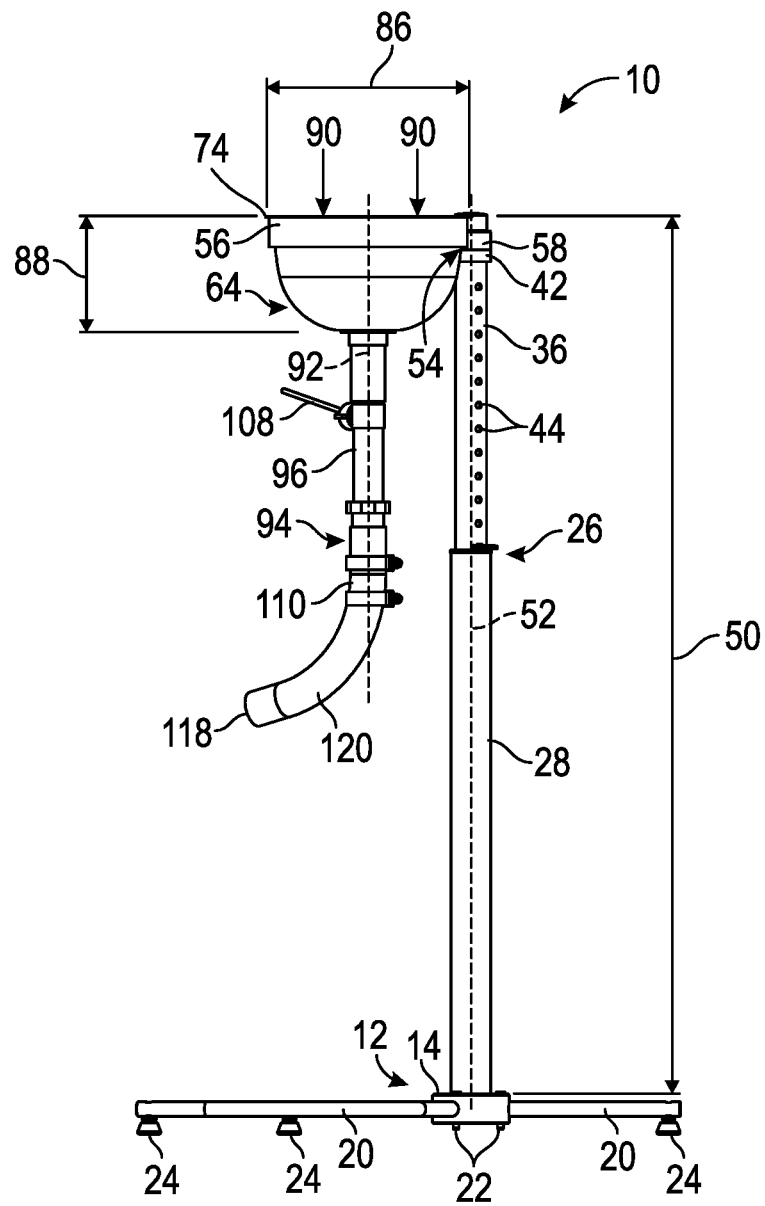
FIG. 3 is a front elevational view of the device shown in FIGS. 1 and 2.
Figure 4:
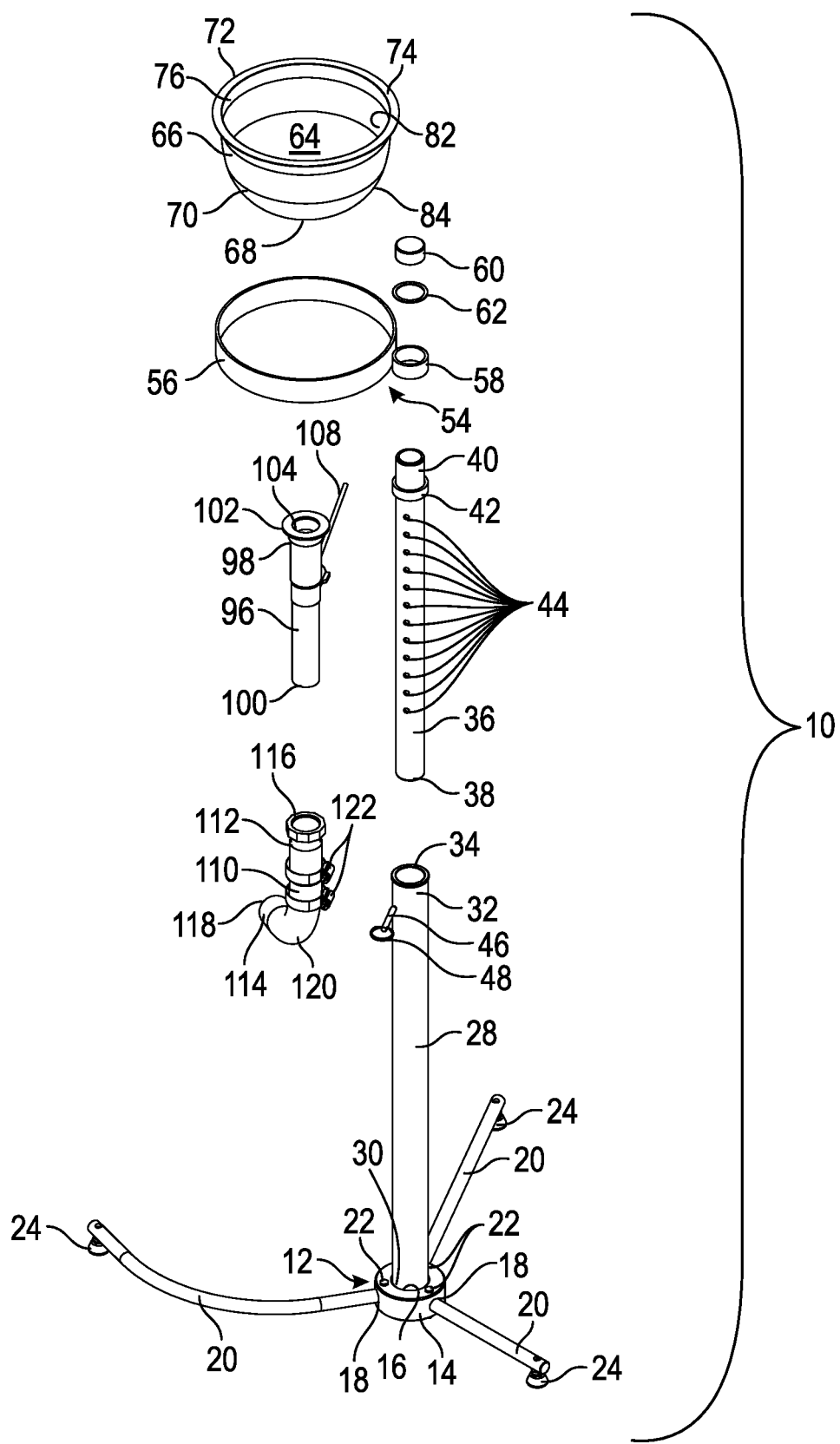
FIG. 4 is an exploded perspective view of the device shown in FIGS. 1-3.
Figure 5:
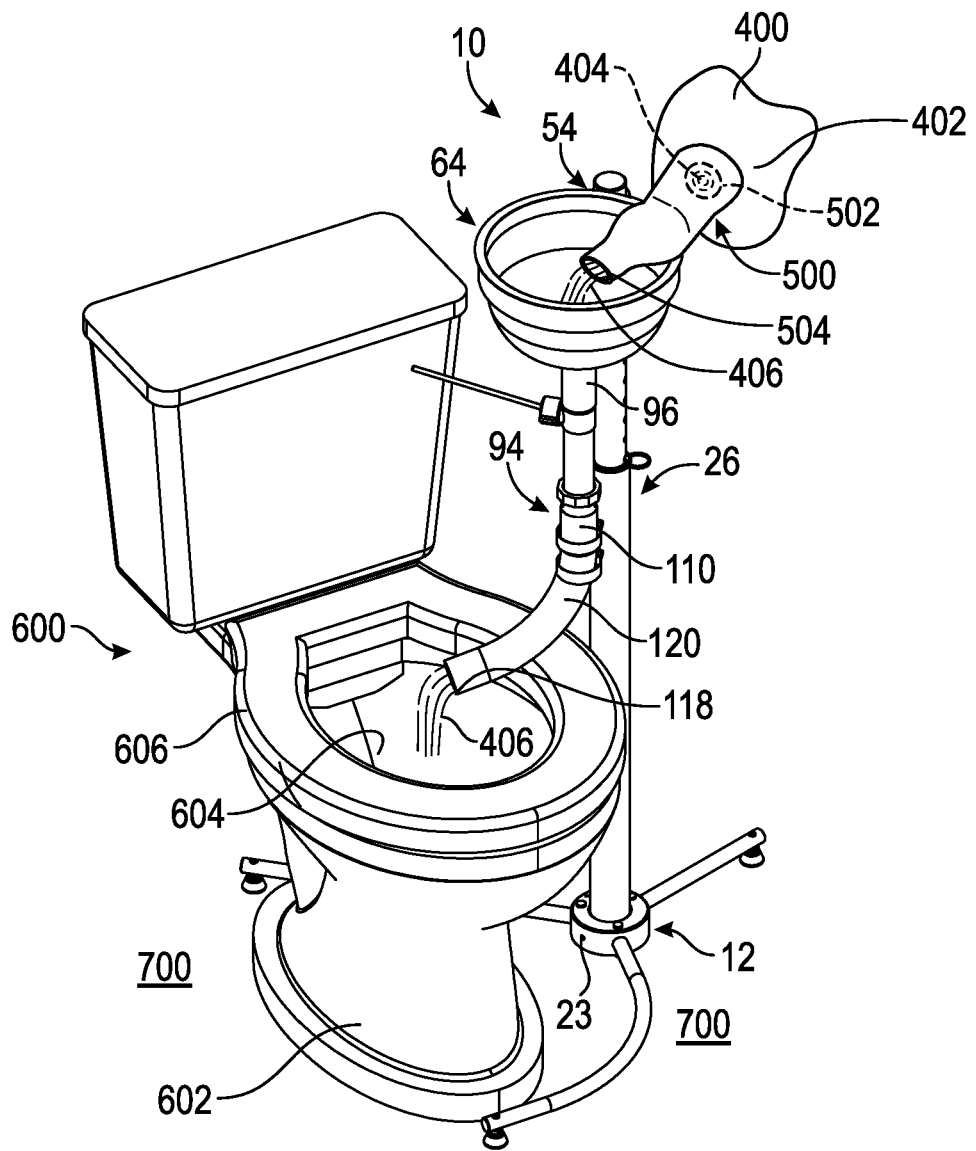
FIG. 5 is a perspective view of the device shown in FIGS. 1-4, illustrating at least a lower drain portion of a drain of the device positioned over a toilet bowl opening of a toilet while the device is in use.
Figure 6:
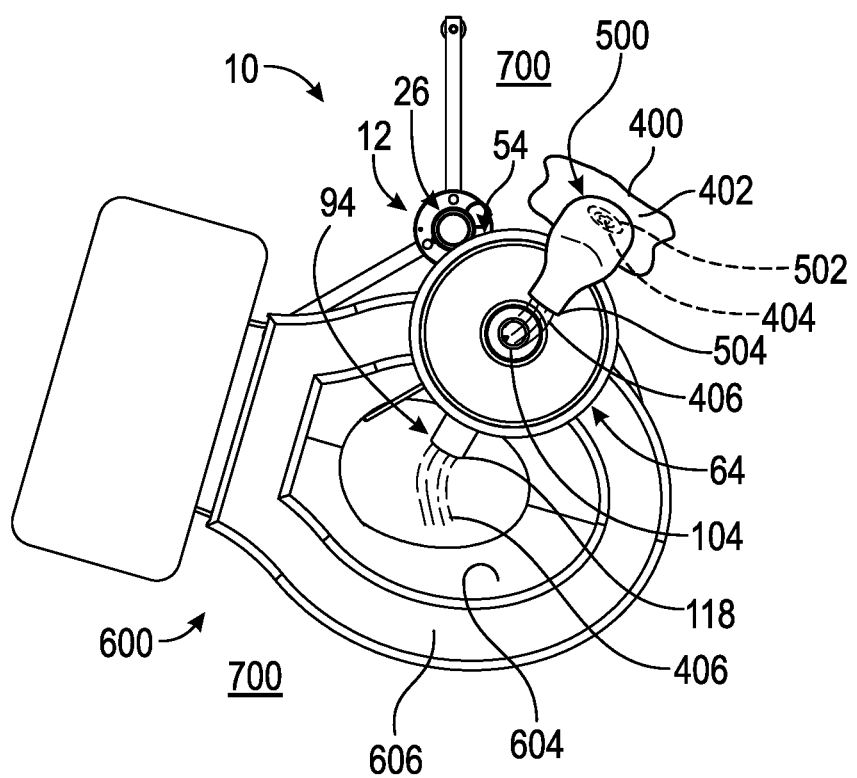
FIG. 6 is a top plan view of the device shown in FIGS. 1-5, further illustrating at least the lower drain portion of the drain positioned over the toilet bowl opening of the toilet shown in FIG. 5 while the device is in use.
Figure 7:
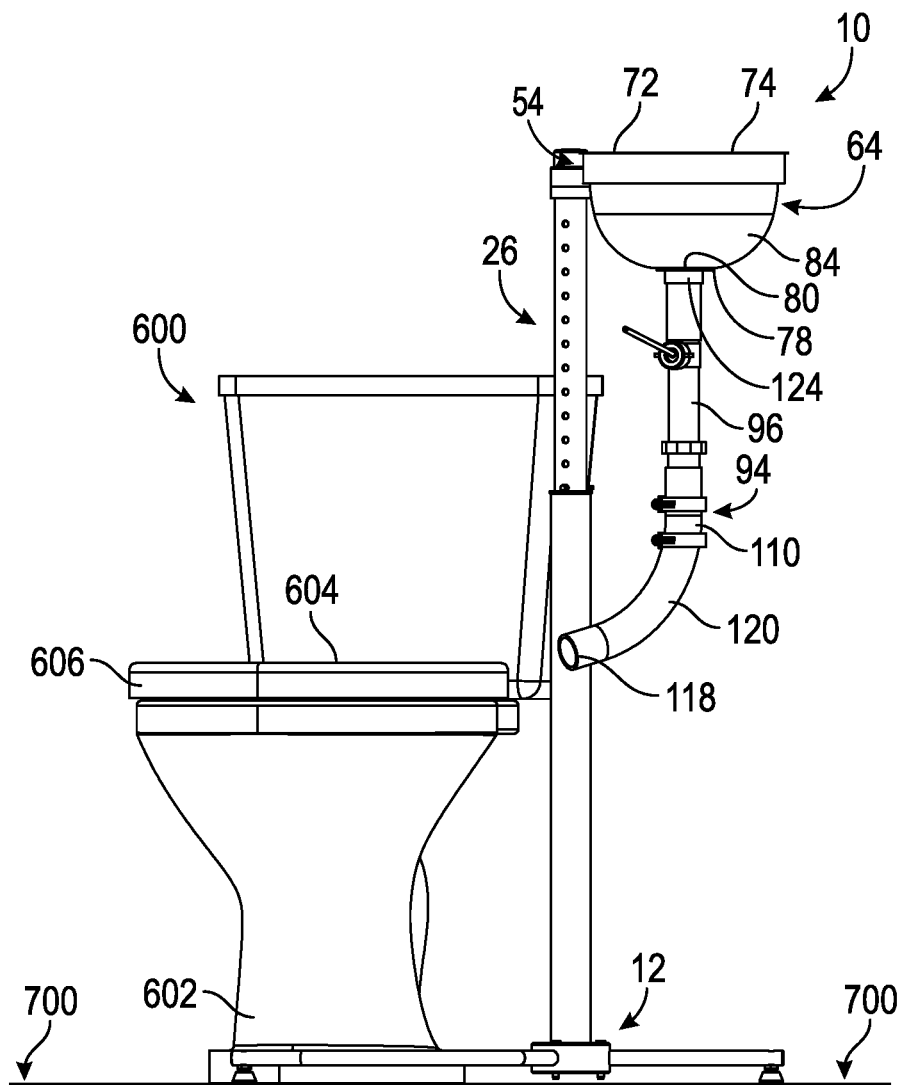
FIG. 7 is a front elevational view of the device shown in FIGS. 1-6, illustrating at least the lower drain portion of the drain positioned away from the toilet bowl opening of the toilet shown in FIGS. 5 and 6 while the device is not in use.

As shown in FIGS. 1-7, the device 10 includes a base 12. As will be further discussed herein, since the device 10 is portable, the base 12 may be supported on a floor 700, such as the floor of a room or space (e.g., a bathroom or restroom) in which the toilet 600 is located. In this regard, when the device 10 is installed adjacent to the toilet 600 (e.g., as shown in FIGS. 5-7), the base 12 is not configured to be mounted on a vertical wall (e.g., a surrounding vertical wall or partition) in the room or space in which the toilet 600 is located.

The base 12 includes a central portion 14 having a central opening 16 and a plurality of side openings 18 formed therein, as will be further discussed herein. The central portion 14 may be substantially tubular or substantially solid.

Figure 1:
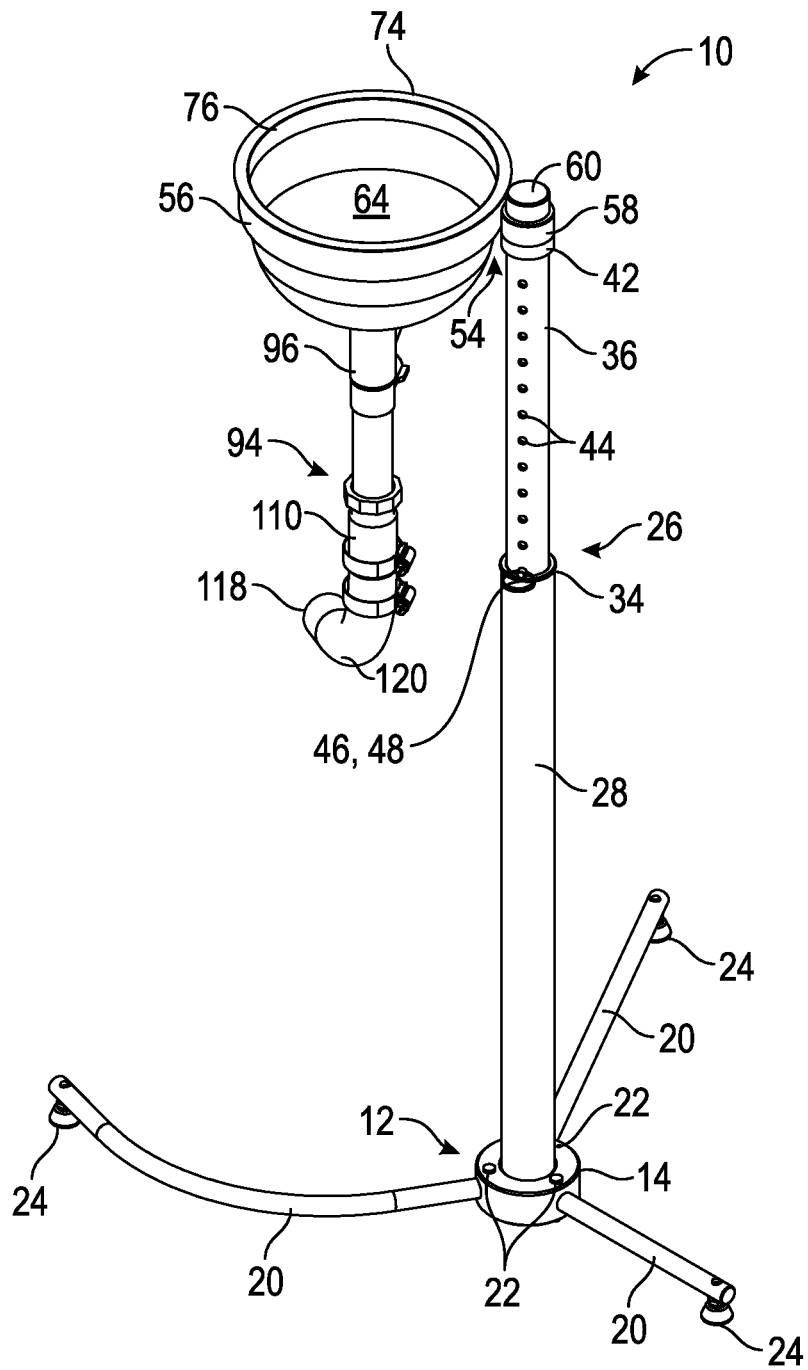
FIG. 1 is a perspective view of one illustrative embodiment of a device for sanitarily draining human waste from an ostomy pouch into a toilet.

The base 12 further includes a plurality of legs 20. Each leg 20 may be elongated and substantially tubular or substantially solid. The plurality of legs 20 are coupled to the central portion 14 so as to extend laterally outwardly from the central portion 14. More specifically, each leg 20 is at least partially disposed within one of the side openings 18 and is removably coupled to the central portion 14 by way of a removable fastener (e.g., a bolt or pin) 22 such that each leg 20 may be quickly and easily decoupled from or coupled to the central portion 14 as desired, such as when the device 10 is to be transported, stored, or installed for use. As shown in FIGS. 1, 5 and 7, at least one of the legs 20 may be generally curved or bent so as to be capable of closely surrounding part of a base 602 of the toilet 600. In this regard, when the device 10 is installed adjacent to the toilet 600, the base 12 may advantageously fit in relatively small or tight spaces defined between the toilet 600 and adjacent walls, partitions, bathtubs, showers, vanities, etc. that may be near the toilet 600. Additionally, each leg 20 includes a foot 24 for engaging the floor 700 such that the base 12 may be stably supported on the floor 700. Each foot 24 may be coupled to each leg 20 (e.g., by a fastener or press fit) or may be formed as an integral part of each leg 20, as may be understood by one skilled in the art.

Regarding overall construction of the base 12, the central portion 14 and each of the legs 20 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art. Moreover, each foot 24 may be made of any suitable material, such as a relatively soft material (e.g., an injection-molded plastic or rubber), such that each foot 24 may be advantageously capable of stabilizing the base 12 while supported on the floor 700 without damaging or scuffing the floor 700, as may be understood by one skilled in the art.

Figure 2:
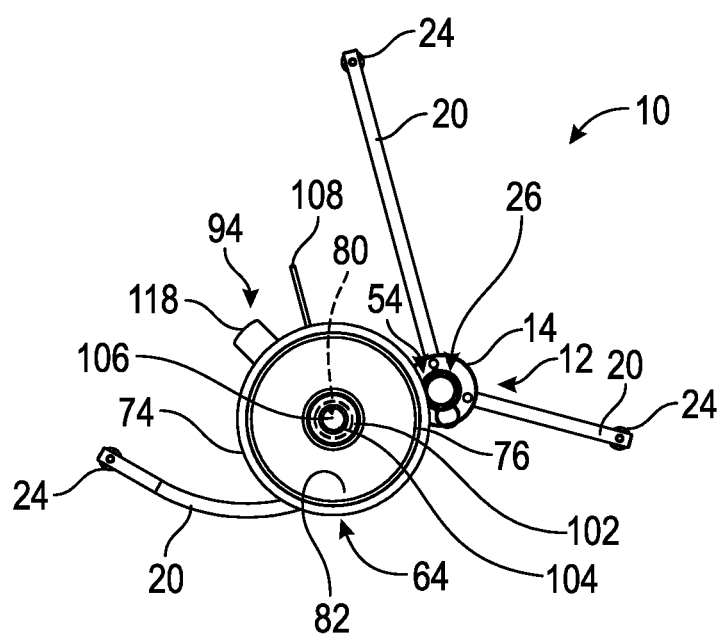
FIG. 2 is a top plan view of the device shown in FIG. 1.

As further shown in FIGS. 1-7, the device 10 further includes a main support 26. The main support 26 includes a lower support portion 28 having a lower end 30 and an upper end 32. As a non-limiting example, the lower support portion 28 may be elongated, substantially tubular, and may be circular in cross-section. Moreover, the lower support portion 28 may be rigid and non-bendable so as to advantageously provide stability to the device 10 while in use. The lower support portion 28 is coupled to the base 12 so as to extend upwardly from the base 12. More specifically, the lower end 30 of the lower support portion 28 is at least partially disposed within the central opening 16 of the central portion 14 of the base 12 and is removably coupled to the central portion 14 by way of a fastener (e.g., a set screw or other fastener as shown in FIG. 5) 23 such that the lower support portion 28 may be quickly and easily decoupled from or coupled to the central portion 14 of the base 12 as desired, such as when the device 10 is to be transported, stored, or installed for use. As shown in FIGS. 1 and 4, a bushing (e.g., a plastic low-friction bushing) 34 is seated within the lower support portion 28 at the upper end 32 thereof, as will be further discussed herein.

The main support 26 further includes an upper support portion 36 having a lower end 38 and an upper end 40. As a non-limiting example, the upper support portion 36 may be elongated, substantially tubular, and may be circular in cross-section. Moreover, the upper support portion 36 may be rigid and non-bendable so as to advantageously provide stability to the device 10 while in use. As will be further discussed herein, as shown in FIG. 4, the upper support portion 36 includes a shoulder 42 coupled thereto proximate the upper end 40 so as to circumscribe or otherwise surround an exterior of the upper support portion 36. Additionally, the upper support portion 36 has a plurality of vertically-aligned side holes 44 formed therein. The upper support portion 36 extends through the bushing 34 and is at least partially disposed within the lower support portion 28 such that the upper support portion 36 is slidably engaged (e.g., telescopically) with the lower support portion 28. In this regard, a removable fastener (e.g., a pin) 46 is inserted into one of the vertically-aligned side holes 44 such that an overall vertical height 50 of the main support 26 may be adjusted along a vertically-extending center axis 52 of the main support 26. Moreover, as shown in FIGS. 1, 3 and 5, an outwardly-protruding portion 48 of the removable fastener 46 may be supported on the upper end 32 of the lower support portion 28 once the removable fastener 46 is inserted into one of the vertically-aligned side holes 44 to maintain the adjusted overall vertical height 50 of the main support 26. In this regard, the upper support portion 36 may be advantageously grasped and lifted to slide upwardly or pivot with respect to the lower support portion 28, or may be removed from the lower support portion 28 entirely, without the need to remove the removable fastener 46 from the upper support portion 36.

Regarding overall construction of the main support 26, the lower support portion 28 and the upper support portion 36 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 1-7, the device 10 further includes a holder 54. As shown in FIG. 4, the holder 54 includes a holding portion 56 and a coupling portion 58 fixed to the holding portion 56. As a non-limiting example, the holding portion 56 and the coupling portion 58 may each be ring-shaped and may abut each other in a fixed, side-by-side manner. Additionally, as shown in FIGS. 3 and 7, part of the coupling portion 58 may be disposed lower than the holding portion 56. Moreover, the ring-shape of the holding portion 56 may be substantially larger in diameter than the ring-shape of the coupling portion 58. The holding portion 56 and the coupling portion 58 may be formed as separate pieces before being fixed to each other, or may be monolithically formed together as a single piece, as may be understood by one skilled in the art.

As shown in FIGS. 1, 3, 5 and 7, the holder 54 is pivotally coupled to the main support 26. More specifically, the coupling portion 58 of the holder 54 is pivotally coupled to the upper support portion 36 of the main support 26 proximate the upper end 40 of the upper support portion 36. In this regard, at least part of the upper support portion 36 extends through the coupling portion 58 such that the coupling portion 58 is pivotally supported on the shoulder 42 of the upper support portion 36 so as to circumscribe or otherwise surround the exterior of the upper support portion 36. As shown in FIG. 4, a cap 60 and a washer 62 are coupled at or proximate the upper end of the upper support portion 36 of the main support 26, above and proximate the coupling portion 58 of the holder 54, such that the coupling portion 58 is stably maintained on the shoulder 42 of the upper support portion 36 while pivotally coupled to the upper support portion 36. In this regard, as will be further discussed herein, with the coupling portion 58 of the holder 54 pivotally coupled to the main support 26, the holding portion 56 of the holder 54 is disposed laterally outboard of the coupling portion 58 and the entire holder 54 may be pivoted about the vertically-extending center axis 52 of the main support 26.

Regarding overall construction of the holder 54, the holding portion 56 and the coupling portion 58 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 1-7, the device 10 further includes a basin 64. As shown in FIGS. 2-4 and 7, the basin 64 has an upper portion 66, a lower portion 68, and an intermediate portion 70 disposed between the upper portion 66 and the lower portion 68. The upper portion 66 of the basin 64 has a top end 72 having a top lip (e.g., an annular edge) 74 forming a top opening 76 therein, and the lower portion 68 of the basin 64 has a bottom end 78 having a bottom opening 80 formed therein. As a non-limiting example, the basin 64 may be bowl-shaped, which may be particularly advantageous as will be further discussed herein. In this regard, the basin 64 may have a generally concave inner surface 82 extending from the top end 72 to the bottom end 78 and entirely around the basin 64, and an opposing generally convex outer surface 84 extending from the top end 72 to the bottom end 78 and entirely around the basin 64. Additionally, the top lip 74 may be ring-shaped, may be oriented substantially horizontally, and may extend entirely around the top end 72 of the basin 64. Moreover, an overall lateral width (i.e., diameter) 86 of the basin 64 may be greater than an overall vertical height (i.e., depth) 88 of the basin 64, which may be particularly advantageous as will be further discussed herein.

As shown in FIGS. 1-3 and 5-7, the basin 64 is retained by the holder 54 such that the basin 64 is operably coupled to the main support 26 by way of the holder 54. More specifically, the basin 64 is inserted into the holding portion 56 of the holder 54 such that at least part of the upper portion 66 of the basin 64 is seated or otherwise disposed within the holding portion 56 and the top lip 74 of the basin 64 engages the holding portion 56. In this regard, the top lip 74 of the basin 64 is supported by the holding portion 56 of the holder 54 such that at least the weight 90 of the basin 64 is applied to the holder 54 by way of at least the top lip 74, thereby advantageously stably maintaining the basin 64 within the holding portion 56 while being retained by the holder 54, yet advantageously allowing the basin 64 to be quickly and easily lifted and removed entirely from the holder 54 as desired while the holder 54 remains pivotally coupled to the main support 26. Additionally, as further shown in FIGS. 1-3 and 5-7, since the upper portion 66 of the basin 64 is at least partially circumscribed or otherwise surrounded by the holding portion 56 of the holder 54 at a location above the lower portion 68 of the basin 64, the basin 64 advantageously maintains a stabilizing lower center of gravity within the holding portion 56 while being retained by the holder 54. Moreover, as will be further discussed herein, with the basin 64 retained by the holding portion 56 of the holder 54, a vertically-extending center axis 92 of the basin 64 is laterally offset from, and parallel to, the vertically-extending center axis 52 of the main support 26. In this regard, as shown in FIG. 3, the basin 64, together with the holder 54, may be pivoted about the vertically-extending center axis 52 of the main support 26.

While not shown, in an alternative configuration, the holder 54 includes the coupling portion 58 without the holding portion 56, and the coupling portion 58 is fixed directly to the basin 64 (e.g., to the upper portion 66 of the basin 64 in a fixed, side-by-side manner) such that the coupling portion 58 of the holder 54 operably couples the basin 64 to the main support 26, as may be understood by one skilled in the art.

Regarding overall construction of the basin 64, the basin 64 may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 1-7, the device 10 further includes a drain 94. As shown in FIG. 4, the drain 94 includes an upper drain portion 96. As a non-limiting example, the upper drain portion 96 may be generally elongated, substantially tubular, and may be circular in cross-section. Additionally, the upper drain portion 96 has an upper end 98 and a lower end 100. The upper end 98 has a flange 102 forming a drain inlet 104 therein. Moreover, as shown in FIG. 2, the upper drain portion 96 includes a valve 106 disposed at least partially therein. The valve 106 is operably coupled to a pivot rod 108 extending generally laterally outwardly from the upper drain portion 96. As will be further discussed herein, the valve 106 may be opened or closed by lowering or lifting the pivot rod 108, as may be understood by one skilled in the art.

While not shown, in an alternative configuration, the valve 106 may be replaced with a pop-up stopper (not shown) which is operably coupled to the pivot rod 108. The pop-up stopper is disposed at least partially within the upper drain portion 96 of the drain 94 and protrudes upwardly above the flange 102 such that the pop-up stopper may be opened (i.e., in an upward position above the flange 102, thereby allowing the drain inlet 104 to remain open) or closed (i.e., in a downward position sealed against the flange 102, thereby closing the drain inlet 104) by lowering or lifting the pivot rod 108, as may be understood by one skilled in the art.

The drain 94 further includes a lower drain portion 110. As a non-limiting example, the lower drain portion 110 may be generally elongated and curved, substantially tubular, and may be circular in cross-section. Additionally, the lower drain portion 110 has an upper end 112 and a lower end 114. The upper end 112 has a slip joint 116 coupled thereto and the lower end 114 has a drain outlet 118 formed therein. Moreover, as will be further discussed herein, a lower part 120 of the lower drain portion 110 curves generally downwardly and terminates at the lower end 114 of the lower drain portion 110.

As shown in FIGS. 1, 3, 5 and 7, the lower drain portion 110 of the drain 94 is removably coupled to the upper drain portion 96 of the drain 94, by way of the slip joint 116 and a plurality of band clamps (e.g., hose clamps) 122, which may be particularly advantageous as will be further discussed herein. In this regard, the lower drain portion 110 is removably coupled to the upper drain portion 96 in a sealed, water-tight manner such that the lower drain portion 110 is in fluid communication with the upper drain portion 96.

As shown in FIGS. 2, 3, 6 and 7, the drain 94 is coupled to the basin 64 at the bottom opening 80 of the basin 64 such that the drain 94 is in fluid communication with the basin 64. In this regard, the flange 102 of the upper drain portion 96 of the drain 94 is coupled to the bottom end 78 of the basin 64 at the bottom opening 80 of the basin 64 in a sealed, water-tight manner. More specifically, a sealant or gasket (not shown) is disposed between the flange 102 and the bottom end 78 of the basin 64 and a threaded nut 124 (e.g., as shown in FIG. 7) is tightened on threads (not shown) of the upper drain portion 96, below and against the bottom end 78 of the basin 64, such that the flange 102 is coupled (i.e., in the sealed, water-tight manner) to the bottom end 78 of the basin 64 and the drain inlet 104 of the upper drain portion 96 is disposed at the bottom opening 80 of the basin 64. As shown in FIGS. 1, 3, 5 and 7, with the drain 94 coupled to basin 64 and with the basin 64 retained by the holder 54, the basin 64 and the drain 94, together with the holder 54, may be pivoted about the vertically-extending center axis 52 of the main support 26. Moreover, with the drain 94 coupled to the basin 64 and with the basin 64 retained by the holder 54, the basin 64 and the drain 94 together may be quickly and easily lifted and removed entirely from the holder 54 (e.g., with the drain 94 being lifted upwardly through the holding portion 56 of the holder 54) as desired while the holder 54 remains pivotally coupled to the main support 26. In this regard, once the basin 64 has been lifted upwardly and removed entirely from the holder 54, the basin 64 may be further lifted and tilted at various angles such that the drain 94 may be lifted upwardly through, and removed entirely from, the holding portion 56 of the holder 54, which may be particularly advantageous as will be further discussed herein.

Regarding overall construction of the drain 94, the upper drain portion 96 thereof may be made of any suitable material (e.g., stainless steel, brass, aluminum, fiber reinforced plastic, etc.) by way of any suitable manufacturing process (e.g., casting, stamping, extrusion, machining, welding, injection molding, etc.), as may be understood by one skilled in the art. Moreover, the lower drain portion 110 of the drain 94 may be made of any suitable material (e.g., rigid or flexible plastic, rubber, etc.) by way of any suitable manufacturing process (e.g., extrusion, injection molding, etc.), as may be understood by one skilled in the art.

Figure 20:
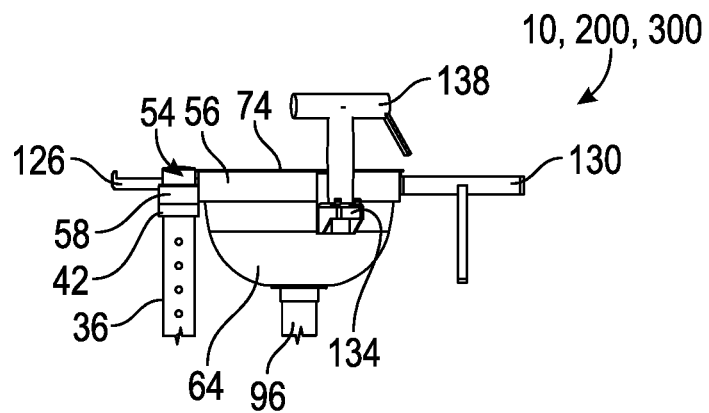
FIG. 20 is a partial front elevational view of the respective devices shown in FIGS. 1-7, 8-13 and 14-19, illustrating various examples of accessories of the respective devices.
Figure 21:
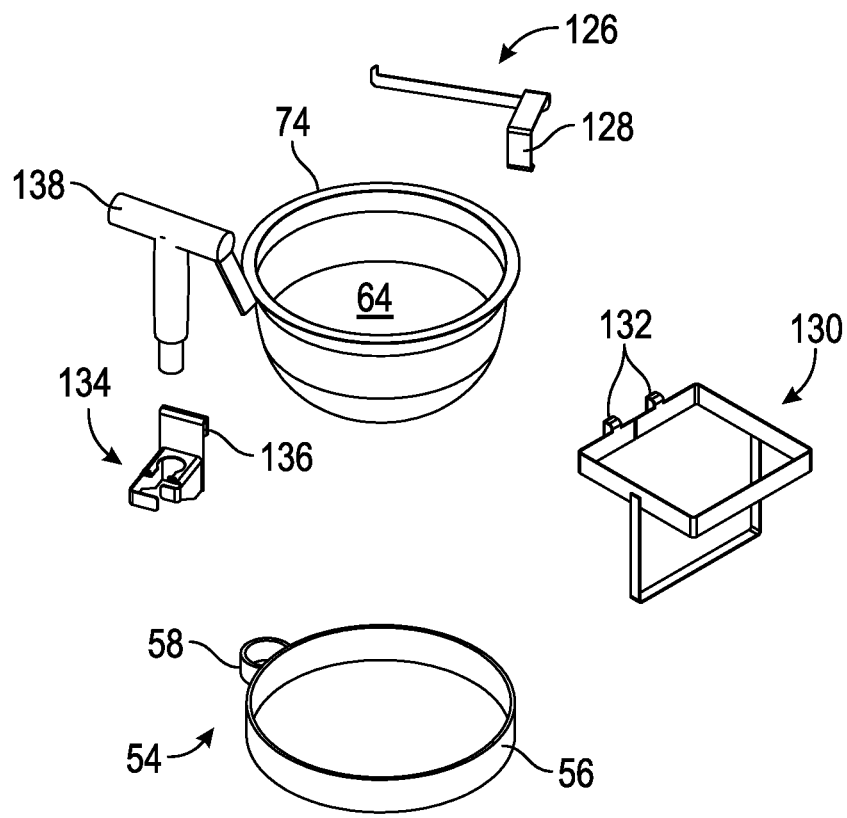
FIG. 21 is a partial exploded perspective view of the respective devices shown in FIGS. 1-7, 8-13 and 14-19, further illustrating the various accessories of the respective devices shown in FIG. 20.

As shown in FIGS. 20 and 21, the device 10 optionally further includes at least one accessory for advantageously providing additional conveniences while using the device 10. As a non-limiting example, the at least one accessory may be at least one or more of a toilet paper holder 126 for holding a roll of toilet paper (not shown), a tissue box holder 130 for holding a tissue box (not shown) and a sprayer holder 134 for holding a sprayer 138 (e.g., which may be connected to a hose (not shown) connected directly or indirectly to a toilet water supply valve (not shown), depending on the number of water connections the toilet water supply valve may have and whether or not an intermediate hose splitter (not shown) is employed). Other accessories may also be included, as may be understood by one skilled in the art.

As further shown in FIGS. 20 and 21, the toilet paper holder 126 includes a coupling portion 128 that engages the holding portion 56 of the holder 54 such that the toilet paper holder 126 is retained by the holder 54 proximate the basin 64 (i.e., adjacent to the upper portion 66 of the basin 64 and at least partially beneath the top lip 74 of the basin 64). Additionally, the tissue box holder 130 includes one or more coupling portions 132 that engage the holding portion 56 of the holder 54 such that the tissue box holder 130 is retained by the holder 54 proximate the basin 64 (i.e., adjacent to the upper portion 66 of the basin 64 and at least partially beneath the top lip 74 of the basin 64). Moreover, the sprayer holder 134 includes a coupling portion 136 that engages the holding portion 56 of the holder 54 such that the sprayer holder 134 is retained by the holder 54 proximate the basin 64 (i.e., adjacent to the upper portion 66 of the basin 64 and at least partially beneath the top lip 74 of the basin 64). In this regard, with any of the toilet paper holder 126, the tissue box holder 130 and the sprayer holder 134 retained by the holding portion 56 of the holder 54, the top lip 74 of the basin 64 advantageously stably maintains any of the toilet paper holder 126, the tissue box holder 130 and the sprayer holder 134 on the holder 54 since at least the weight 90 of the basin 64, and therefore the additional weight of the drain 94 as well, is applied to any of the toilet paper holder 126, the tissue box holder 130 and the sprayer holder 134, and therefore to the holder 54 as well, by way of at least the top lip 74, as previously discussed herein.

Regarding overall construction of the at least one accessory, any of the toilet paper holder 126, the tissue box holder 130 and the sprayer holder 134 may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

Referring to FIGS. 5-7, overall use of the device 10, including the draining of the human waste 406 from the ostomy pouch 500 into the toilet 600, will now be described in detail. The device 10 is installed adjacent to the toilet 600 such that the base 12 of the device 10 is supported on the floor 700 of the room or space in which the toilet 600 is located.

As shown in FIGS. 5 and 6, with a toilet seat 606 of the toilet 600 lowered or with the toilet seat 606 raised (not shown), a person 400 may pivot the basin 64 and the drain 94, together with the holder 54, about the main support 26 (i.e., towards the toilet 600 and about the vertically-extending center axis 52 of the main support 26) such that at least the lower part 120 of the lower drain portion 110 of the drain 94 (i.e., which includes the drain outlet 118) is positioned over a toilet bowl opening 604 of the toilet 600. Regarding the person 400, it is to be understood that merely a portion of the person 400, which includes at least part of an abdomen 402 having a stoma 404, is schematically shown. Additionally, the ostomy pouch 500 (i.e., that needs draining) containing the human waste 406 therein is schematically shown. The ostomy pouch 500 is temporarily secured to the abdomen 402 of the person 400 such that an inlet 502 of the ostomy pouch 500, disposed at an attachment end of the ostomy pouch 500, is secured around the stoma 404, thereby allowing the human waste 406 to flow out of the stoma 404 and be collected and temporarily stored within the ostomy pouch 500.

As further shown in FIGS. 5 and 6, to drain the human waste 406 from the ostomy pouch 500 into the toilet 600, the person 400 may stand proximate the basin 64 of the device 10 while the ostomy pouch 500 remains secured to the abdomen 402 of the person 400. In this regard, the person 400 may therefore stand in a relaxed, upright position, thereby advantageously avoiding the need to stand over the toilet 600, sit on the toilet 600, straddle the toilet 600, or kneel on the floor 700 next to the toilet 600. Preferably, the top end 72 of the basin 64 is disposed at a height below at least a portion of the ostomy pouch 500 such that the ostomy pouch 500 slopes generally downwardly when a closure end (i.e., sometimes referred to as a tail) of the ostomy pouch 500 is positioned over the top opening 76 of the basin 64 (i.e., to better facilitate draining the human waste 406 from the ostomy pouch 500). In this regard, if needed, the person 400 may adjust the height of the basin 64 by adjusting the overall vertical height 50 of the main support 26 (i.e., in a manner as previously discussed herein) since the basin 64 is retained by the holder 54 which is pivotally coupled to the main support 26.

As further shown in FIGS. 5 and 6, the person 400 may then position the closure end of the ostomy pouch 500 over the top opening 76 of the basin 64 and preferably at least partially within the basin 64. In this regard, since the overall lateral width 86 of the basin 64 may be greater than the overall vertical height 88 of the basin 64 (i.e., as previously discussed herein), the top end 72 of the basin 64, including the top opening 76 of the basin 64, may advantageously provide a relatively wide space (i.e., target area) for the person 400 to drain the ostomy pouch 500, thereby advantageously reducing the likelihood of the human waste 406 spilling or splashing outside of the basin 64. The person 400 may then open the closure end of the ostomy pouch 500 such that an outlet 504 of the ostomy pouch 500 is open. In this regard, the human waste 406 temporarily stored within the ostomy pouch 500 may then freely drain from the ostomy pouch 500 such that the human waste 406 flows out of the outlet 504 of the ostomy pouch 500 and into the basin 64. Moreover, since the basin 64 may be bowl-shaped (i.e., as previously discussed herein), the human waste 406 received within the basin 64 from the ostomy pouch 500 may advantageously flow downwardly within the basin 64 in a relatively efficient, unimpeded manner (i.e., with reduced drag as a result of the bowl-shape of the basin 64), thereby advantageously further reducing the likelihood of the human waste 406 spilling or splashing outside of the basin 64. In this regard, with the valve 106 of the drain 94 open, the human waste 406 received within the basin 64 from the ostomy pouch 500 may flow downwardly into the drain inlet 104 of the drain 94 such that the drain 94 directs and drains any human waste 406 received from the basin 64 into the toilet 600 (i.e., by way of the human waste 406 exiting the drain outlet 118 of the drain 94).

Once the human waste 406 is entirely drained from the ostomy pouch 500, with the valve 106 of the drain 94 open or closed, and with the ostomy pouch 500 still secured to the abdomen 402 of the person 400 or with the ostomy pouch 500 removed from the abdomen 402, the person 400 may advantageously wash or otherwise sanitize the ostomy pouch 500 (e.g., such as with the sprayer 138, as previously discussed herein) within the basin 64 before reattaching (i.e., if removed) the ostomy pouch 500 to the abdomen 402 or reclosing the closure end of the ostomy pouch 500 such that the outlet 504 of the ostomy pouch 500 is closed. In this regard, with the valve 106 of the drain 94 open, any water or other substance used to wash or otherwise sanitize the ostomy pouch 500 is advantageously directed and drained into the toilet 600 by way of the drain 94. Additionally, the person 400 may advantageously wash or otherwise sanitize the device 10, including the basin 64 and the drain 94 (e.g., such as with the sprayer 138, as previously discussed herein), while at least the lower part 120 of the lower drain portion 110 of the drain 94 remains positioned over the toilet bowl opening 604 of the toilet 600. Moreover, as previously discussed herein, if desired, the person 400 may advantageously (i.e., quickly and easily) lift and remove the basin 64 and the drain 94 entirely from the holder 54 while the holder 54 remains pivotally coupled to the main support 26 such that at least the basin 64 and the drain 94 may be washed or otherwise sanitized at a location away from the toilet 600.

As shown in FIG. 7, when the device 10 is not in use, the person 400 or other person may pivot the basin 64 and the drain 94, together with the holder 54, about the main support 26 (i.e., away from the toilet 600 in a manner opposite of the manner previously discussed herein) such that at least the lower drain portion 110 of the drain 94 is positioned away from the toilet bowl opening 604 of the toilet 600, thereby advantageously allowing people that may not require use of the device 10 to gain unobstructed access to the toilet 600.

Referring to FIGS. 8-13, 20 and 21, another illustrative embodiment of a device 200 for sanitarily draining human waste (e.g., feces, urine, etc.) 406 from an ostomy pouch 500 into a toilet 800 will now be described in detail. The device 200 may include many of the same components or features included as part of the device 10, as previously described herein in detail. In this regard, any component or feature of the device 200 which may be the same as a particular component or feature of the device 10 will be referred to with the same reference numeral as previously set forth herein, as may be understood by one skilled in the art.

As shown in FIGS. 8-13, the device 200 includes a base 202. As will be further discussed herein, since the device 200 is installable on the toilet 800 (e.g., as shown in FIGS. 10-13), the base 202 is not configured to be mounted on a vertical wall (e.g., a surrounding vertical wall or partition) in a room or space in which the toilet 800 is located. In this regard, as will be further discussed herein, one primary difference between the device 200 and the device 10 is that the base 202 of the device 200 is toilet-mountable whereas the device 10 includes the portable base 12 which may be supported on the floor 700 (e.g., in a manner as previously discussed herein).

Figure 9:
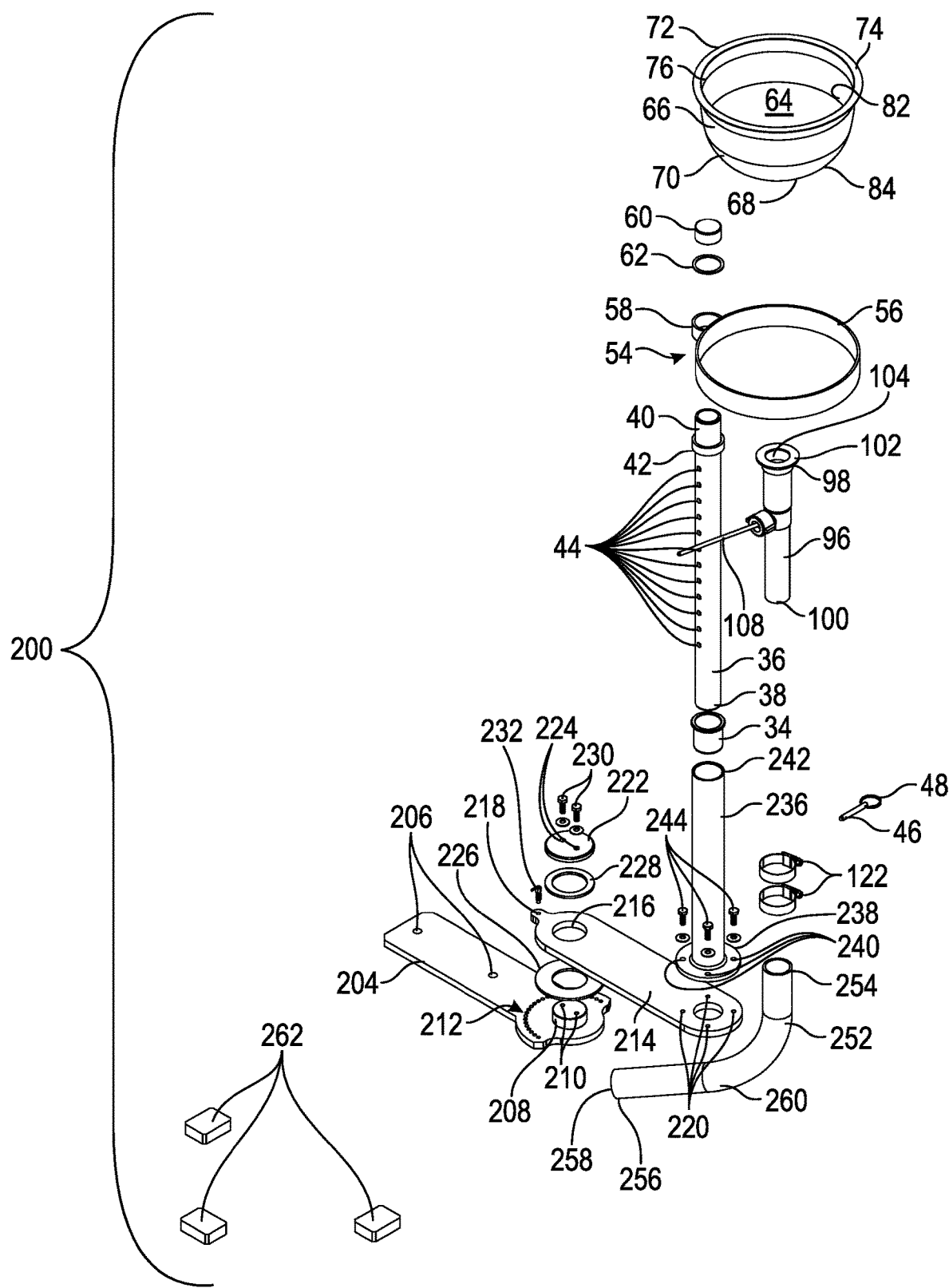
FIG. 9 is an exploded perspective view of the device shown in FIG. 8.
Figure 11:
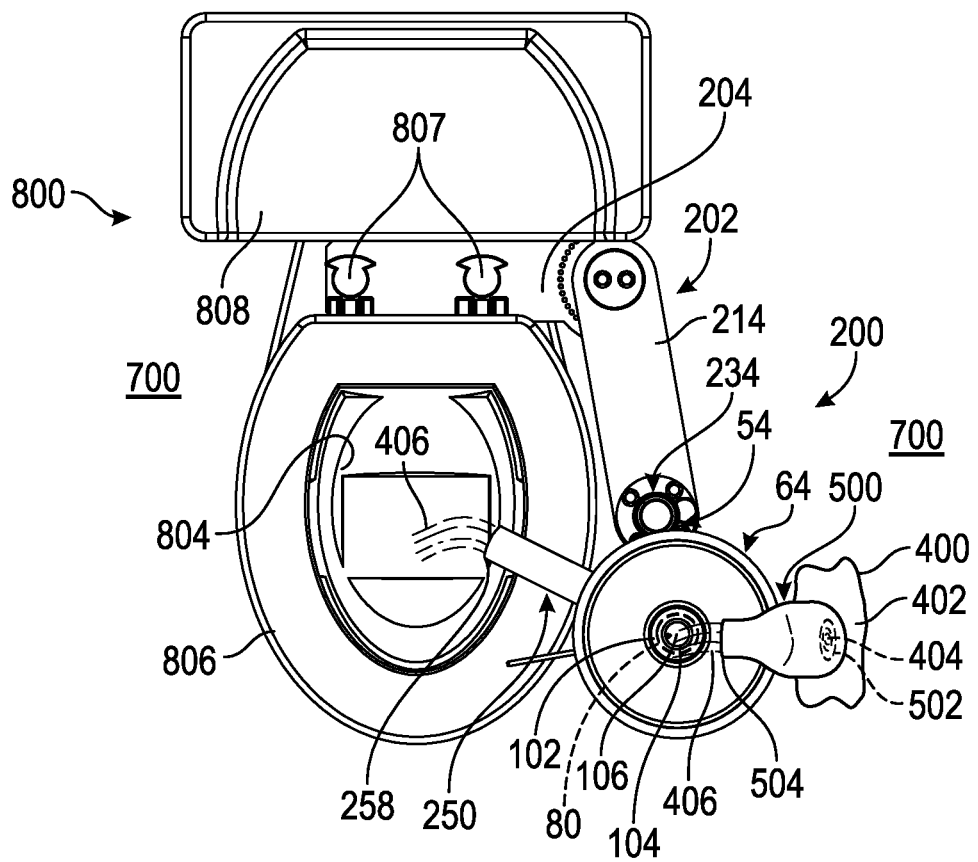
FIG. 11 is a top plan view of the device shown in FIGS. 8-10, further illustrating the device mounted on the toilet shown in FIG. 10 and at least the lower drain portion of the drain positioned over the toilet bowl opening of the toilet while the device is in use.
Figure 12:
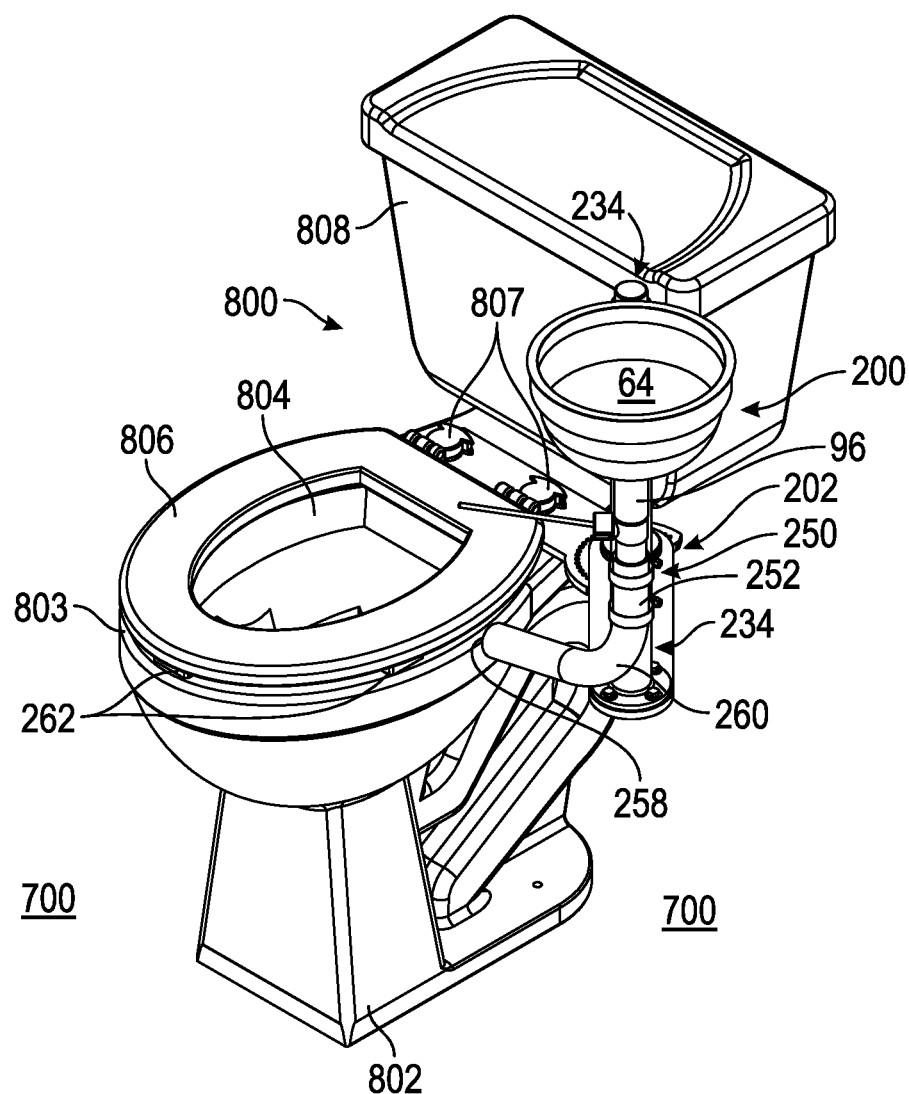
FIG. 12 is a perspective view of the device shown in FIGS. 8-11, illustrating the device mounted on the toilet shown in FIGS. 10 and 11 and at least the lower drain portion of the drain positioned away from the toilet bowl opening of the toilet while the device is not in use.

The base 202 includes a stationary portion 204. As shown in FIG. 9, the stationary portion 204 may be substantially flat. The stationary portion 204 has a pair of mounting holes 206 formed therein. The pair of mounting holes 206 may be spaced apart from each other at a standard width or distance (e.g., corresponding to a pair of toilet seat mounting holes (not shown) of standardized toilets, such as the toilet 800) such that the stationary portion 204 may be mounted on the toilet 800 beneath a pair of toilet seat mounting portions 807 of a toilet seat 806 of the toilet 800 by way of fasteners (e.g., bolts secured with nuts (not shown)) disposed within and extending downwardly through the pair of toilet seat mounting portions 807, the pair of mounting holes 206, and the pair of toilet seat mounting holes (not shown) of the toilet 800, as may be understood by one skilled in the art. In this regard, as shown in FIGS. 11 and 12, the stationary portion 204 of the base 202 is mounted on a base 802 of the toilet 800 rearward of a toilet bowl opening 804 formed in the base 802 and forward of a tank 808 of the toilet 800. As further shown in FIG. 9, the stationary portion 204 further includes a pivot 208 protruding upwardly from the stationary portion 204. The pivot 208 may be substantially cylindrical and has a plurality of threaded fastener-receiving holes 210 formed therein, as will be further discussed herein. Additionally, the stationary portion 204 further has a plurality of arcuately-aligned holes 212 formed therein, as will be further discussed herein. As further shown in FIG. 9, the plurality of arcuately-aligned holes 212 are disposed adjacent to the pivot 208 of the stationary portion 204.

The base 202 further includes an arm portion 214. As shown in FIG. 9, the arm portion 214 may be substantially flat. As will be further discussed herein, the arm portion 214 has a pivot-receiving opening 216 formed therein (e.g., which may be circular), a threaded locking element-receiving hole 218 formed therein, and a plurality of threaded fastener-receiving holes 220 formed therein.

Figure 8:
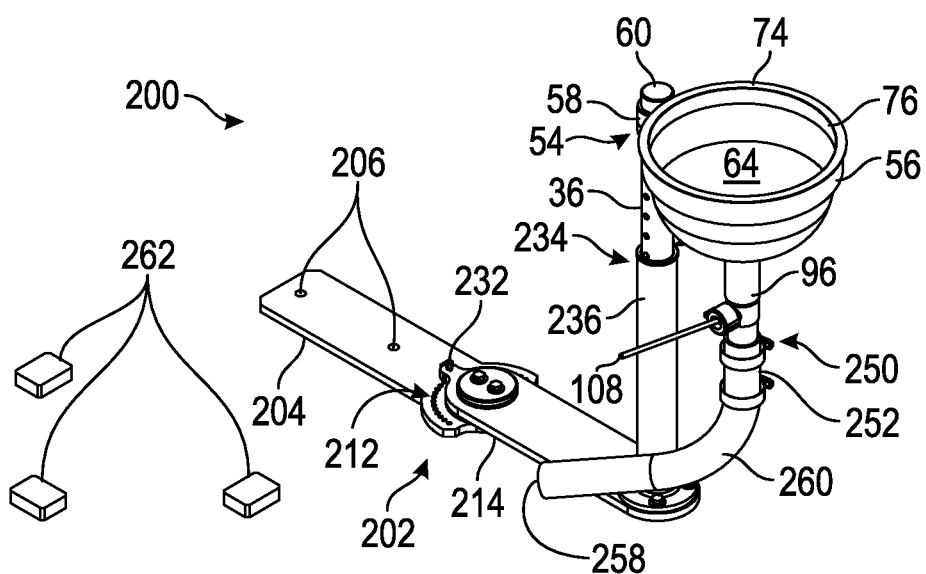
FIG. 8 is a perspective view of another illustrative embodiment of a device for sanitarily draining human waste from an ostomy pouch into a toilet.
Figure 13:
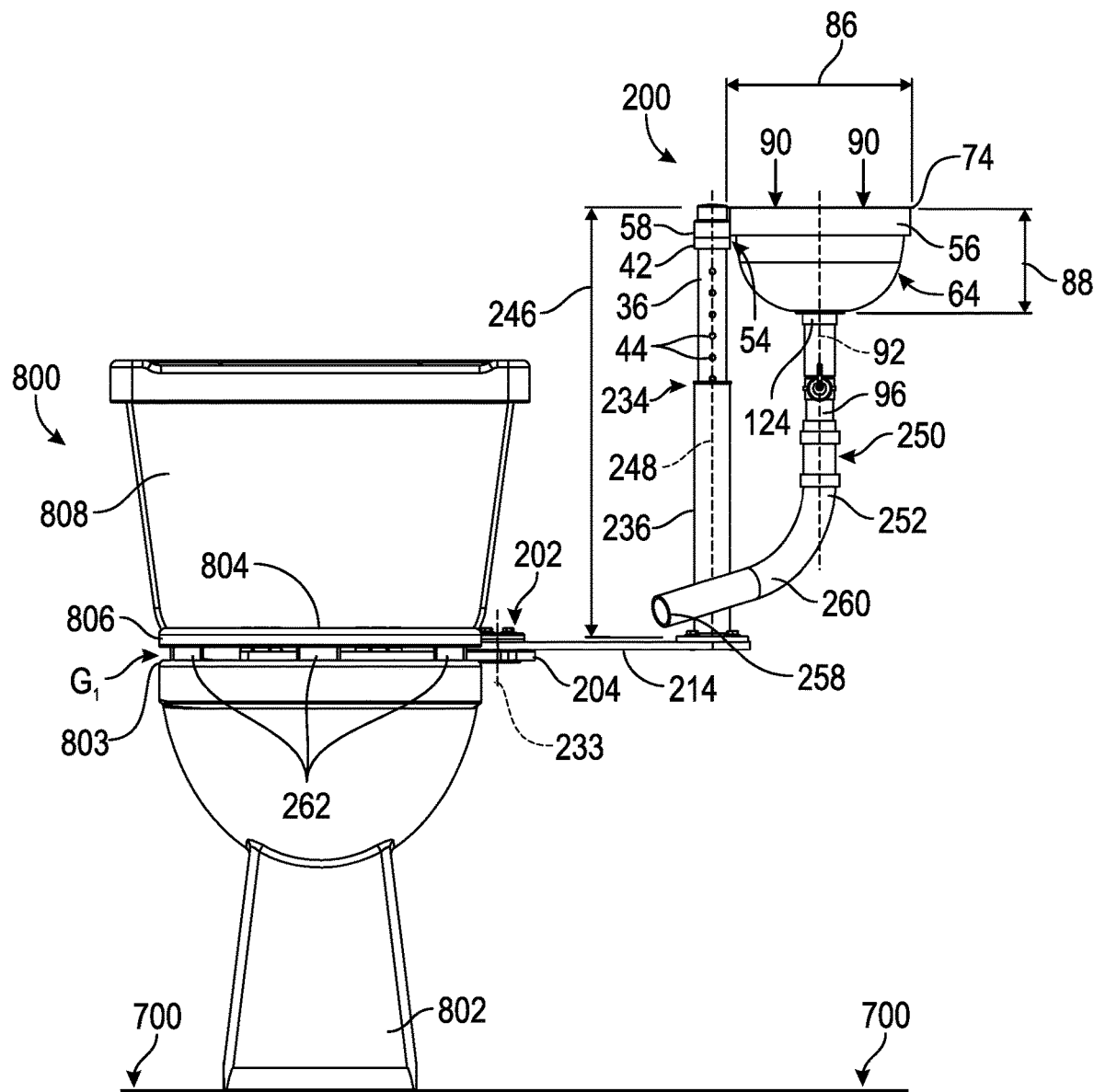
FIG. 13 is a front elevational view of the device shown in FIGS. 8-12, further illustrating the device mounted on the toilet shown in FIGS. 10-12 and at least the lower drain portion of the drain positioned away from the toilet bowl opening of the toilet while the device is not in use.

As shown in FIGS. 8, 9 and 13, the arm portion 214 of the base 202 is pivotally coupled to the stationary portion 204 of the base 202 so as to extend laterally outwardly from the stationary portion 204. More specifically, as a non-limiting example, the base 202 further includes a cap plate 222 having a plurality of fastener-receiving holes 224 formed therein, an annular lower flat bushing (e.g., made of a low-friction plastic) 226, an annular upper flat bushing (e.g., made of a low-friction plastic) 228, and a plurality of threaded fasteners (e.g., bolts with washers) 230. As shown in FIGS. 8 and 9, the pivot 208 of the stationary portion 204 is disposed within and extends through the pivot-receiving opening 216 formed in the arm portion 214, with the annular lower flat bushing 226 disposed around the pivot 208 beneath the arm portion 214 and with the annular upper flat bushing 228 disposed around the pivot 208 above the arm portion 214. The cap plate 222 is disposed over the annular upper flat bushing 228 and is coupled to the pivot 208 by way of the plurality of threaded fasteners 230 extending through the plurality of fastener-receiving holes 224 formed in the cap plate 222 and being secured within the plurality of threaded fastener-receiving holes 210 formed in the pivot 208, thereby pivotally coupling the arm portion 214 of the base 202 to the stationary portion 204 of the base 202. In this regard, as shown in FIG. 13, the arm portion 214 may be pivoted about the pivot 208 of the stationary portion 204 about a vertically-extending pivot axis 233 in a smooth, low-friction manner (i.e., as a result of the annular lower flat bushing 226 being disposed between the stationary portion 204 and the arm portion 214, and the annular upper flat bushing 228 being disposed between the arm portion 214 and the cap plate 222).

As further shown in FIGS. 8-13, and shown in FIGS. 8 and 9, the arm portion 214 of the base 202 may be pivoted and locked into one of a plurality of different positions with respect to the stationary portion 204 of the base 202. More specifically, as a non-limiting example, the base 202 further includes a locking element (e.g., a threaded indexing plunger having an internal spring-loaded pin (not shown) retractable by a knob or other pull) 232 secured within the threaded locking element-receiving hole 218 formed in the arm portion 214 such that the internal spring-loaded pin thereof extends into one of the plurality of arcuately-aligned holes 212 formed in the stationary portion 204. As will be further discussed herein, the locking element 232 may be pulled and held such that the internal spring-loaded pin thereof is retracted from one of the plurality of arcuately-aligned holes 212 formed in the stationary portion 204. The arm portion 214 may then be pivoted about the pivot 208 of the stationary portion 204 (i.e., about the vertically-extending pivot axis 233) until the arm portion 214 is in a desired position (i.e., corresponding to one of the plurality of arcuately-aligned holes 212) with respect to the stationary portion 204. Once the arm portion 214 is in the desired position, the locking element 232 may be released and lowered such that the internal spring-loaded pin thereof extends into one of the plurality of arcuately-aligned holes 212, thereby locking the arm portion 214 of the base 202 into the desired position with respect to the stationary portion 204 of the base 202.

Regarding overall construction of the base 202, the stationary portion 204 and the arm portion 214 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 8-13, the device 200 further includes a main support 234. The main support 234 includes a lower support portion 236 having a lower end 238 and an upper end 242. As a non-limiting example, the lower support portion 236 may be elongated, substantially tubular, and may be circular in cross-section. Moreover, the lower support portion 236 may be rigid and non-bendable so as to advantageously provide stability to the device 200 while in use. As shown in FIG. 9, the lower end 238 of the lower support portion 236 is in the form of a flange having a plurality of fastener-receiving holes 240 formed therein. In this regard, the lower support portion 236 is coupled to the base 202 so as to extend upwardly from the base 202. More specifically, the lower end 238 of the lower support portion 236 is coupled to the arm portion 214 of the base 202 by way of a plurality of threaded fasteners (e.g., bolts with washers) 244 extending through the plurality of fastener-receiving holes 240 formed in the lower end 238 and being secured within the plurality of threaded fastener-receiving holes 220 formed in the arm portion 214. As further shown in FIG. 9, a bushing (e.g., a plastic low-friction bushing) 34 is seated within the lower support portion 236 at the upper end 242 thereof, as will be further discussed herein.

The main support 234 further includes an upper support portion 36 having a lower end 38 and an upper end 40. As a non-limiting example, the upper support portion 36 may be elongated, substantially tubular, and may be circular in cross-section. Moreover, the upper support portion 36 may be rigid and non-bendable so as to advantageously provide stability to the device 200 while in use. As will be further discussed herein, as shown in FIG. 9, the upper support portion 36 includes a shoulder 42 coupled thereto proximate the upper end 40 so as to circumscribe or otherwise surround an exterior of the upper support portion 36. Additionally, the upper support portion 36 has a plurality of vertically-aligned side holes 44 formed therein. The upper support portion 36 extends through the bushing 34 and is at least partially disposed within the lower support portion 236 such that the upper support portion 36 is slidably engaged (e.g., telescopically) with the lower support portion 236. In this regard, a removable fastener (e.g., a pin) 46 is inserted into one of the vertically-aligned side holes 44 such that an overall vertical height 246 of the main support 234 may be adjusted along a vertically-extending center axis 248 of the main support 234. Moreover, as shown in FIGS. 8 and 9, an outwardly-protruding portion 48 of the removable fastener 46 may be supported on the upper end 242 of the lower support portion 236 once the removable fastener 46 is inserted into one of the vertically-aligned side holes 44 to maintain the adjusted overall vertical height 246 of the main support 234. In this regard, the upper support portion 36 may be advantageously grasped and lifted to slide upwardly or pivot with respect to the lower support portion 236, or may be removed from the lower support portion 236 entirely, without the need to remove the removable fastener 46 from the upper support portion 36.

Regarding overall construction of the main support 234, the lower support portion 236 and the upper support portion 36 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 8-13, the device 200 further includes a holder 54. As shown in FIG. 9, the holder 54 includes a holding portion 56 and a coupling portion 58 fixed to the holding portion 56. As a non-limiting example, the holding portion 56 and the coupling portion 58 may each be ring-shaped and may abut each other in a fixed, side-by-side manner. Additionally, as shown in FIG. 13, part of the coupling portion 58 may be disposed lower than the holding portion 56. Moreover, the ring-shape of the holding portion 56 may be substantially larger in diameter than the ring-shape of the coupling portion 58. The holding portion 56 and the coupling portion 58 may be formed as separate pieces before being fixed to each other, or may be monolithically formed together as a single piece, as may be understood by one skilled in the art.

As shown in FIGS. 8, 12 and 13, the holder 54 is pivotally coupled to the main support 234. More specifically, the coupling portion 58 of the holder 54 is pivotally coupled to the upper support portion 36 of the main support 234 proximate the upper end 40 of the upper support portion 36. In this regard, at least part of the upper support portion 36 extends through the coupling portion 58 such that the coupling portion 58 is pivotally supported on the shoulder 42 of the upper support portion 36 so as to circumscribe or otherwise surround the exterior of the upper support portion 36. As shown in FIG. 9, a cap 60 and a washer 62 are coupled at or proximate the upper end of the upper support portion 36 of the main support 234, above and proximate the coupling portion 58 of the holder 54, such that the coupling portion 58 is stably maintained on the shoulder 42 of the upper support portion 36 while pivotally coupled to the upper support portion 36. In this regard, as will be further discussed herein, with the coupling portion 58 of the holder 54 pivotally coupled to the main support 234, the holding portion 56 of the holder 54 is disposed laterally outboard of the coupling portion 58 and the entire holder 54 may be pivoted about the vertically-extending center axis 248 of the main support 234.

Regarding overall construction of the holder 54, the holding portion 56 and the coupling portion 58 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

Figure 10:
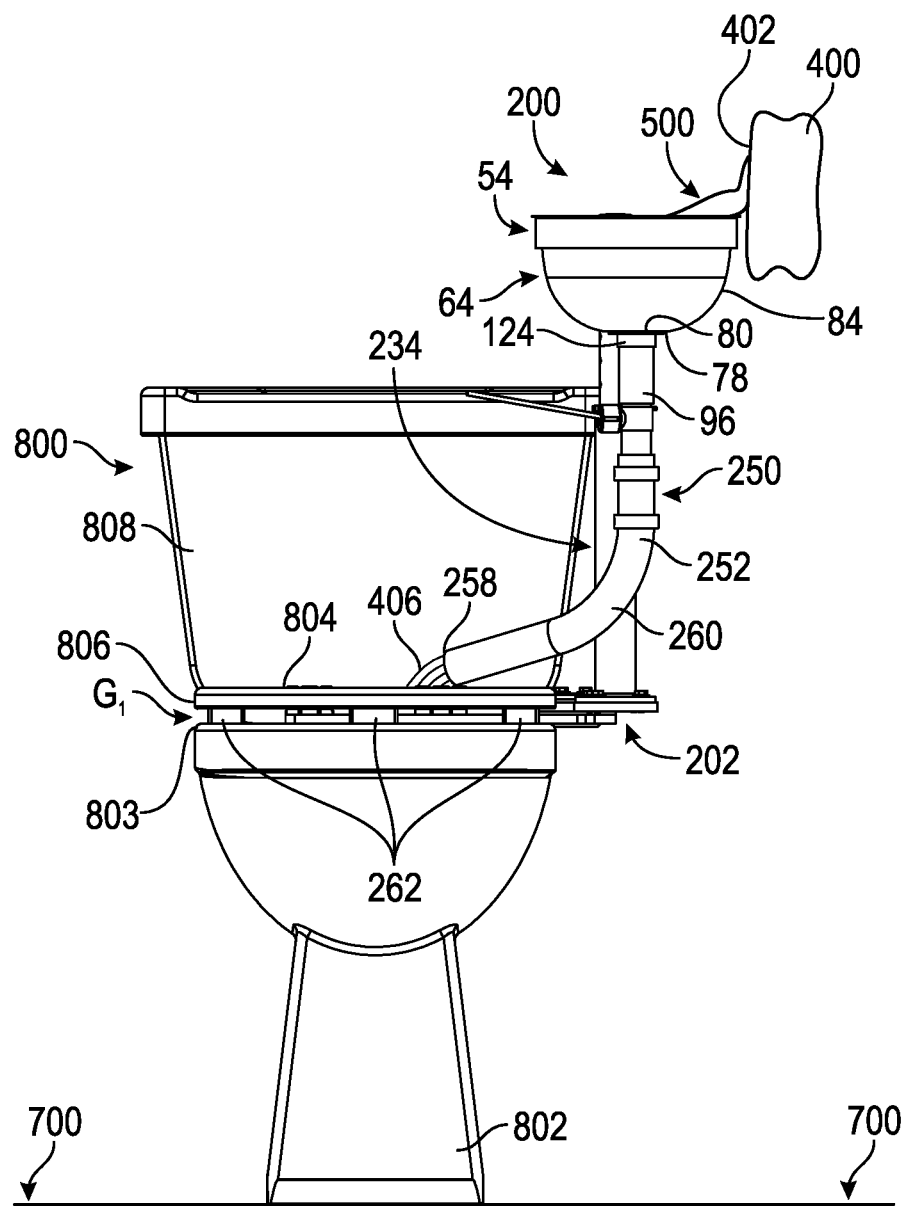
FIG. 10 is a front elevational view of the device shown in FIGS. 8 and 9, illustrating the device mounted on a toilet and at least a lower drain portion of a drain of the device positioned over a toilet bowl opening of the toilet while the device is in use.

As further shown in FIGS. 8-13, the device 200 further includes a basin 64. As shown in FIGS. 9, 10 and 13, the basin 64 has an upper portion 66, a lower portion 68, and an intermediate portion 70 disposed between the upper portion 66 and the lower portion 68. The upper portion 66 of the basin 64 has a top end 72 having a top lip (e.g., an annular edge) 74 forming a top opening 76 therein, and the lower portion 68 of the basin 64 has a bottom end 78 having a bottom opening 80 formed therein. As a non-limiting example, the basin 64 may be bowl-shaped, which may be particularly advantageous as will be further discussed herein. In this regard, the basin 64 may have a generally concave inner surface 82 extending from the top end 72 to the bottom end 78 and entirely around the basin 64, and an opposing generally convex outer surface 84 extending from the top end 72 to the bottom end 78 and entirely around the basin 64. Additionally, the top lip 74 may be ring-shaped, may be oriented substantially horizontally, and may extend entirely around the top end 72 of the basin 64. Moreover, an overall lateral width (i.e., diameter) 86 of the basin 64 may be greater than an overall vertical height (i.e., depth) 88 of the basin 64, which may be particularly advantageous as will be further discussed herein.

As shown in FIGS. 8 and 10-13, the basin 64 is retained by the holder 54 such that the basin 64 is operably coupled to the main support 234 by way of the holder 54. More specifically, the basin 64 is inserted into the holding portion 56 of the holder 54 such that at least part of the upper portion 66 of the basin 64 is seated or otherwise disposed within the holding portion 56 and the top lip 74 of the basin 64 engages the holding portion 56. In this regard, the top lip 74 of the basin 64 is supported by the holding portion 56 of the holder 54 such that at least the weight 90 of the basin 64 is applied to the holder 54 by way of at least the top lip 74, thereby advantageously stably maintaining the basin 64 within the holding portion 56 while being retained by the holder 54, yet advantageously allowing the basin 64 to be quickly and easily lifted and removed entirely from the holder 54 as desired while the holder 54 remains pivotally coupled to the main support 234. Additionally, as further shown in FIGS. 8 and 10-13, since the upper portion 66 of the basin 64 is at least partially circumscribed or otherwise surrounded by the holding portion 56 of the holder 54 at a location above the lower portion 68 of the basin 64, the basin 64 advantageously maintains a stabilizing lower center of gravity within the holding portion 56 while being retained by the holder 54. Moreover, as will be further discussed herein, with the basin 64 retained by the holding portion 56 of the holder 54, a vertically-extending center axis 92 of the basin 64 is laterally offset from, and parallel to, the vertically-extending pivot axis 233 of the base 202 and the vertically-extending center axis 248 of the main support 234. In this regard, as shown in FIG. 13, the basin 64, together with the holder 54, may be pivoted about the vertically-extending center axis 248 of the main support 234. Moreover, as further shown in FIG. 13, the basin 64, together with the holder 54 and the main support 234, may be pivoted about the vertically-extending pivot axis 233 of the base 202 when the arm portion 214 of the base 202 is pivoted with respect to the stationary portion 204 of the base 202.

While not shown, in an alternative configuration, the holder 54 includes the coupling portion 58 without the holding portion 56, and the coupling portion 58 is fixed directly to the basin 64 (e.g., to the upper portion 66 of the basin 64 in a fixed, side-by-side manner) such that the coupling portion 58 of the holder 54 operably couples the basin 64 to the main support 234, as may be understood by one skilled in the art.

Regarding overall construction of the basin 64, the basin 64 may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 8-13, the device 200 further includes a drain 250. As shown in FIG. 9, the drain 250 includes an upper drain portion 96. As a non-limiting example, the upper drain portion 96 may be generally elongated, substantially tubular, and may be circular in cross-section. Additionally, the upper drain portion 96 has an upper end 98 and a lower end 100. The upper end 98 has a flange 102 forming a drain inlet 104 therein. Moreover, as shown in FIG. 11, the upper drain portion 96 includes a valve 106 disposed at least partially therein. The valve 106 is operably coupled to a pivot rod 108 extending generally laterally outwardly from the upper drain portion 96. As will be further discussed herein, the valve 106 may be opened or closed by lowering or lifting the pivot rod 108, as may be understood by one skilled in the art.

While not shown, in an alternative configuration, the valve 106 may be replaced with a pop-up stopper (not shown) which is operably coupled to the pivot rod 108. The pop-up stopper is disposed at least partially within the upper drain portion 96 of the drain 250 and protrudes upwardly above the flange 102 such that the pop-up stopper may be opened (i.e., in an upward position above the flange 102, thereby allowing the drain inlet 104 to remain open) or closed (i.e., in a downward position sealed against the flange 102, thereby closing the drain inlet 104) by lowering or lifting the pivot rod 108, as may be understood by one skilled in the art.

The drain 250 further includes a lower drain portion 252. As a non-limiting example, the lower drain portion 252 may be generally elongated and curved, substantially tubular, and may be circular in cross-section. Additionally, the lower drain portion 252 has an upper end 254 and a lower end 256. The lower end 256 of the lower drain portion 252 has a drain outlet 258 formed therein. Moreover, as will be further discussed herein, a lower part 260 of the lower drain portion 252 curves generally downwardly and terminates at the lower end 256 of the lower drain portion 252. In this regard, the lower drain portion 252 may be curved and shaped the same as the lower drain portion 110 of the device 10 or may be curved and shaped slightly differently (e.g., as shown in FIGS. 8-13), as may be understood by one skilled in the art.

As shown in FIGS. 8, 10, 12 and 13, the lower drain portion 252 of the drain 250 is removably coupled to the upper drain portion 96 of the drain 250, by way of a plurality of band clamps (e.g., hose clamps) 122, which may be particularly advantageous as will be further discussed herein. In this regard, the lower drain portion 252 is removably coupled to the upper drain portion 96 in a sealed, water-tight manner such that the lower drain portion 252 is in fluid communication with the upper drain portion 96. Moreover, since each device 10, 200 may include the same upper drain portion 96, 96 (i.e., as previously described herein for each device 10, 200) and the respective lower drain portions 110, 252 of each device 10, 200 are each be removably coupled to the respective upper drain portions 96, 96 of each device 10, 200, the lower drain portions 110, 252 may therefore be advantageously interchangeable on each device 10, 200, as may be understood by one skilled in the art.

As shown in FIGS. 10, 11 and 13, the drain 250 is coupled to the basin 64 at the bottom opening 80 of the basin 64 such that the drain 250 is in fluid communication with the basin 64. In this regard, the flange 102 of the upper drain portion 96 of the drain 250 is coupled to the bottom end 78 of the basin 64 at the bottom opening 80 of the basin 64 in a sealed, water-tight manner. More specifically, a sealant or gasket (not shown) is disposed between the flange 102 and the bottom end 78 of the basin 64 and a threaded nut 124 (e.g., as shown in FIGS. 10 and 13) is tightened on threads (not shown) of the upper drain portion 96, below and against the bottom end 78 of the basin 64, such that the flange 102 is coupled (i.e., in the sealed, water-tight manner) to the bottom end 78 of the basin 64 and the drain inlet 104 of the upper drain portion 96 is disposed at the bottom opening 80 of the basin 64. As shown in FIGS. 8, 10, 12 and 13, with the drain 250 coupled to basin 64 and with the basin 64 retained by the holder 54, the basin 64 and the drain 250, together with the holder 54, may be pivoted about the vertically-extending center axis 248 of the main support 234. Additionally, as further shown in FIGS. 8, 10, 12 and 13, with the drain 250 coupled to basin 64 and with the basin 64 retained by the holder 54, the basin 64 and the drain 250, together with the holder 54 and the main support 234, may be pivoted about the vertically-extending pivot axis 233 of the base 202 when the arm portion 214 of the base 202 is pivoted with respect to the stationary portion 204 of the base 202. Moreover, with the drain 250 coupled to the basin 64 and with the basin 64 retained by the holder 54, the basin 64 and the drain 250 together may be quickly and easily lifted and removed entirely from the holder 54 (e.g., with the drain 250 being lifted upwardly through the holding portion 56 of the holder 54) as desired while the holder 54 remains pivotally coupled to the main support 234. In this regard, once the basin 64 has been lifted upwardly and removed entirely from the holder 54, the basin 64 may be further lifted and tilted at various angles such that the drain 250 may be lifted upwardly through, and removed entirely from, the holding portion 56 of the holder 54, which may be particularly advantageous as will be further discussed herein.

Regarding overall construction of the drain 250, the upper drain portion 96 thereof may be made of any suitable material (e.g., stainless steel, brass, aluminum, fiber reinforced plastic, etc.) by way of any suitable manufacturing process (e.g., casting, stamping, extrusion, machining, welding, injection molding, etc.), as may be understood by one skilled in the art. Moreover, the lower drain portion 252 of the drain 250 may be made of any suitable material (e.g., rigid or flexible plastic, rubber, etc.) by way of any suitable manufacturing process (e.g., extrusion, injection molding, etc.), as may be understood by one skilled in the art.

As shown in FIGS. 8-10, 12 and 13, the device 200 further includes a plurality of toilet seat spacers (e.g., in the form of injection-molded plastic blocks) 262. As previously discussed herein, the stationary portion 204 of the base 202 of the device 200 may be mounted on the toilet 800 beneath the pair of toilet seat mounting portions 807 of the toilet seat 806 of the toilet 800. In this regard, as shown in FIGS. 10, 12 and 13, a gap $G_1$ may therefore be defined between the lowered toilet seat 806 and at least a toilet bowl rim 803 (i.e., which surrounds the toilet bowl opening 804) of the base 802 of the toilet 800. As a result of the gap $G_1$ being defined, the toilet seat 806 could slope downwardly and bend in an unlevel manner when lowered (i.e., possibly causing unwanted stress on the pair of toilet seat mounting portions 807 of the toilet seat 806). In this regard, as further shown in FIGS. 10, 12 and 13, the plurality of toilet seat spacers 262 are secured to the toilet seat 806 or to the toilet bowl rim 803 (e.g., by way of an adhesive or an adhesive tape) such that the toilet seat spacers 262 are disposed within the gap $G_1$ and the toilet seat 806 is advantageously stable and level when lowered without causing possible unwanted stress on the pair of toilet seat mounting portions 807 of the toilet seat 806, as may be understood by one skilled in the art.

While not shown, in an alternative configuration, the plurality of toilet seat spacers 262 and the toilet seat 806 are monolithically formed together as a single piece (e.g., by way of injection molding), as may be understood by one skilled in the art.

As shown in FIGS. 20 and 21, the device 200 optionally further includes at least one accessory for advantageously providing additional conveniences while using the device 200. As a non-limiting example, the at least one accessory may be at least one or more of a toilet paper holder 126 for holding a roll of toilet paper (not shown), a tissue box holder 130 for holding a tissue box (not shown) and a sprayer holder 134 for holding a sprayer 138 (e.g., which may be connected to a hose (not shown) connected directly or indirectly to a toilet water supply valve (not shown), depending on the number of water connections the toilet water supply valve may have and whether or not an intermediate hose splitter (not shown) is employed). Other accessories may also be included, as may be understood by one skilled in the art.

As further shown in FIGS. 20 and 21, the toilet paper holder 126 includes a coupling portion 128 that engages the holding portion 56 of the holder 54 such that the toilet paper holder 126 is retained by the holder 54 proximate the basin 64 (i.e., adjacent to the upper portion 66 of the basin 64 and at least partially beneath the top lip 74 of the basin 64). Additionally, the tissue box holder 130 includes one or more coupling portions 132 that engage the holding portion 56 of the holder 54 such that the tissue box holder 130 is retained by the holder 54 proximate the basin 64 (i.e., adjacent to the upper portion 66 of the basin 64 and at least partially beneath the top lip 74 of the basin 64). Moreover, the sprayer holder 134 includes a coupling portion 136 that engages the holding portion 56 of the holder 54 such that the sprayer holder 134 is retained by the holder 54 proximate the basin 64 (i.e., adjacent to the upper portion 66 of the basin 64 and at least partially beneath the top lip 74 of the basin 64). In this regard, with any of the toilet paper holder 126, the tissue box holder 130 and the sprayer holder 134 retained by the holding portion 56 of the holder 54, the top lip 74 of the basin 64 advantageously stably maintains any of the toilet paper holder 126, the tissue box holder 130 and the sprayer holder 134 on the holder 54 since at least the weight 90 of the basin 64, and therefore the additional weight of the drain 250 as well, is applied to any of the toilet paper holder 126, the tissue box holder 130 and the sprayer holder 134, and therefore to the holder 54 as well, by way of at least the top lip 74, as previously discussed herein.

Regarding overall construction of the at least one accessory, any of the toilet paper holder 126, the tissue box holder 130 and the sprayer holder 134 may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

Referring to FIGS. 10-13, overall use of the device 200, including the draining of the human waste 406 from the ostomy pouch 500 into the toilet 800, will now be described in detail. The device 200 is installed on the toilet 800 by way of the base 202 of the device 200 being mounted on the toilet 800 (i.e., in a manner as previously discussed herein).

As shown in FIGS. 10 and 11, with the toilet seat 806 of the toilet 800 lowered or with the toilet seat 806 raised (not shown), a person 400 may pull and hold the locking element 232 of the base 202 such that the arm portion 214 of the base 202 may then be unlocked (i.e., in a manner as previously discussed herein) and pivoted about the pivot 208 (i.e., towards the toilet 800 and about the vertically-extending pivot axis 233) of the stationary portion 204 of the base 202. In this regard, the basin 64 and the drain 250, together with the holder 54 and the main support 234, may be pivoted towards the toilet 800 when the arm portion 214 is pivoted with respect to the stationary portion 204 such that at least the lower part 260 of the lower drain portion 252 of the drain 250 (i.e., which includes the drain outlet 258) is positioned over the toilet bowl opening 804 of the toilet 800. Moreover, the person 400 may then release the locking element 232 of the base 202 such that the arm portion 214 of the base 202 is locked into the desired position (i.e., in a manner as previously discussed herein) with respect to the stationary portion 204 of the base 202. Regarding the person 400, it is to be understood that merely a portion of the person 400, which includes at least part of an abdomen 402 having a stoma 404, is schematically shown. Additionally, the ostomy pouch 500 (i.e., that needs draining) containing the human waste 406 therein is schematically shown. The ostomy pouch 500 is temporarily secured to the abdomen 402 of the person 400 such that an inlet 502 of the ostomy pouch 500, disposed at an attachment end of the ostomy pouch 500, is secured around the stoma 404, thereby allowing the human waste 406 to flow out of the stoma 404 and be collected and temporarily stored within the ostomy pouch 500.

As further shown in FIGS. 10 and 11, to drain the human waste 406 from the ostomy pouch 500 into the toilet 800, the person 400 may stand proximate the basin 64 of the device 200 while the ostomy pouch 500 remains secured to the abdomen 402 of the person 400. In this regard, the person 400 may therefore stand in a relaxed, upright position, thereby advantageously avoiding the need to stand over the toilet 800, sit on the toilet 800, straddle the toilet 800, or kneel on the floor 700 next to the toilet 800. Preferably, the top end 72 of the basin 64 is disposed at a height below at least a portion of the ostomy pouch 500 such that the ostomy pouch 500 slopes generally downwardly when a closure end (i.e., sometimes referred to as a tail) of the ostomy pouch 500 is positioned over the top opening 76 of the basin 64 (i.e., to better facilitate draining the human waste 406 from the ostomy pouch 500). In this regard, if needed, the person 400 may adjust the height of the basin 64 by adjusting the overall vertical height 246 of the main support 234 (i.e., in a manner as previously discussed herein) since the basin 64 is retained by the holder 54 which is pivotally coupled to the main support 234.

As further shown in FIGS. 10 and 11, the person 400 may then position the closure end of the ostomy pouch 500 over the top opening 76 of the basin 64 and preferably at least partially within the basin 64. In this regard, since the overall lateral width 86 of the basin 64 may be greater than the overall vertical height 88 of the basin 64 (i.e., as previously discussed herein), the top end 72 of the basin 64, including the top opening 76 of the basin 64, may advantageously provide a relatively wide space (i.e., target area) for the person 400 to drain the ostomy pouch 500, thereby advantageously reducing the likelihood of the human waste 406 spilling or splashing outside of the basin 64. The person 400 may then open the closure end of the ostomy pouch 500 such that an outlet 504 of the ostomy pouch 500 is open. In this regard, the human waste 406 temporarily stored within the ostomy pouch 500 may then freely drain from the ostomy pouch 500 such that the human waste 406 flows out of the outlet 504 of the ostomy pouch 500 and into the basin 64. Moreover, since the basin 64 may be bowl-shaped (i.e., as previously discussed herein), the human waste 406 received within the basin 64 from the ostomy pouch 500 may advantageously flow downwardly within the basin 64 in a relatively efficient, unimpeded manner (i.e., with reduced drag as a result of the bowl-shape of the basin 64), thereby advantageously further reducing the likelihood of the human waste 406 spilling or splashing outside of the basin 64. In this regard, with the valve 106 of the drain 250 open, the human waste 406 received within the basin 64 from the ostomy pouch 500 may flow downwardly into the drain inlet 104 of the drain 250 such that the drain 250 directs and drains any human waste 406 received from the basin 64 into the toilet 800 (i.e., by way of the human waste 406 exiting the drain outlet 258 of the drain 250).

Once the human waste 406 is entirely drained from the ostomy pouch 500, with the valve 106 of the drain 250 open or closed, and with the ostomy pouch 500 still secured to the abdomen 402 of the person 400 or with the ostomy pouch 500 removed from the abdomen 402, the person 400 may advantageously wash or otherwise sanitize the ostomy pouch 500 (e.g., such as with the sprayer 138, as previously discussed herein) within the basin 64 before reattaching (i.e., if removed) the ostomy pouch 500 to the abdomen 402 or reclosing the closure end of the ostomy pouch 500 such that the outlet 504 of the ostomy pouch 500 is closed. In this regard, with the valve 106 of the drain 250 open, any water or other substance used to wash or otherwise sanitize the ostomy pouch 500 is advantageously directed and drained into the toilet 800 by way of the drain 250. Additionally, the person 400 may advantageously wash or otherwise sanitize the device 200, including the basin 64 and the drain 250 (e.g., such as with the sprayer 138, as previously discussed herein), while at least the lower part 260 of the lower drain portion 252 of the drain 250 remains positioned over the toilet bowl opening 804 of the toilet 800. Moreover, as previously discussed herein, if desired, the person 400 may advantageously (i.e., quickly and easily) lift and remove the basin 64 and the drain 250 entirely from the holder 54 while the holder 54 remains pivotally coupled to the main support 234 such that at least the basin 64 and the drain 250 may be washed or otherwise sanitized at a location away from the toilet 800.

As shown in FIGS. 12 and 13, when the device 200 is not in use, the person 400 or other person may pull and hold the locking element 232 of the base 202 such that the arm portion 214 of the base 202 may then be unlocked (i.e., in a manner as previously discussed herein) and pivoted (i.e., away from the toilet 800) about the pivot 208 of the stationary portion 204 of the base 202. In this regard, the basin 64 and the drain 250, together with the holder 54 and the main support 234, may be pivoted away from the toilet 800 when the arm portion 214 is pivoted with respect to the stationary portion 204 (i.e., in a manner opposite of the manner previously discussed herein) such that at least the lower drain portion 252 of the drain 250 is positioned away from the toilet bowl opening 804 of the toilet 800, thereby advantageously allowing people that may not require use of the device 200 to gain unobstructed access to the toilet 800.

Referring to FIGS. 14-21, yet another illustrative embodiment of a device 300 for sanitarily draining human waste (e.g., feces, urine, etc.) 406 from an ostomy pouch 500 into a toilet 900 will now be described in detail. The device 300 may include many of the same components or features included as part of the device 10 or the device 200, as previously described herein in detail. In this regard, any component or feature of the device 300 which may be the same as a particular component or feature of the device 10 or the device 200 will be referred to with the same reference numeral as previously set forth herein, as may be understood by one skilled in the art.

As shown in FIGS. 14-19, the device 300 includes a base 302. As will be further discussed herein, since the device 300 is installable on the toilet 900 (e.g., as shown in FIGS. 16-19), the base 302 is not configured to be mounted on a vertical wall (e.g., a surrounding vertical wall or partition) in a room or space in which the toilet 900 is located. In this regard, as will be further discussed herein, one primary difference between the device 300 and the device 10 is that the base 302 of the device 300 is toilet-mountable whereas the device 10 includes the portable base 12 which may be supported on the floor 700 (e.g., in a manner as previously discussed herein). Moreover, as will be further discussed herein, one primary difference between the device 300 and the device 200 is that the base 302 of the device 300 includes an additional component for mounting the base 302 on the toilet 900.

Figure 15:
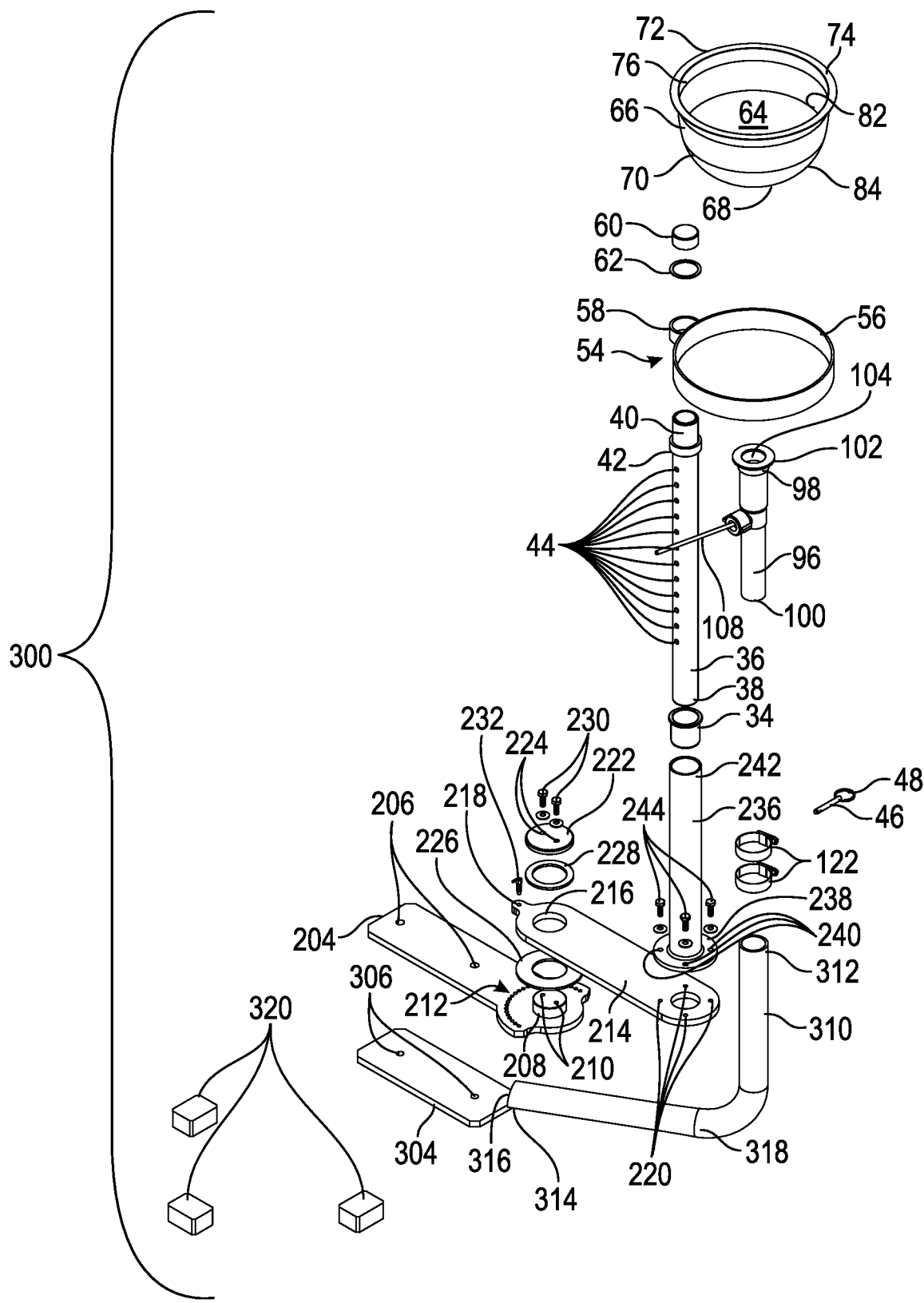
FIG. 15 is an exploded perspective view of the device shown in FIG. 14.
Figure 17:
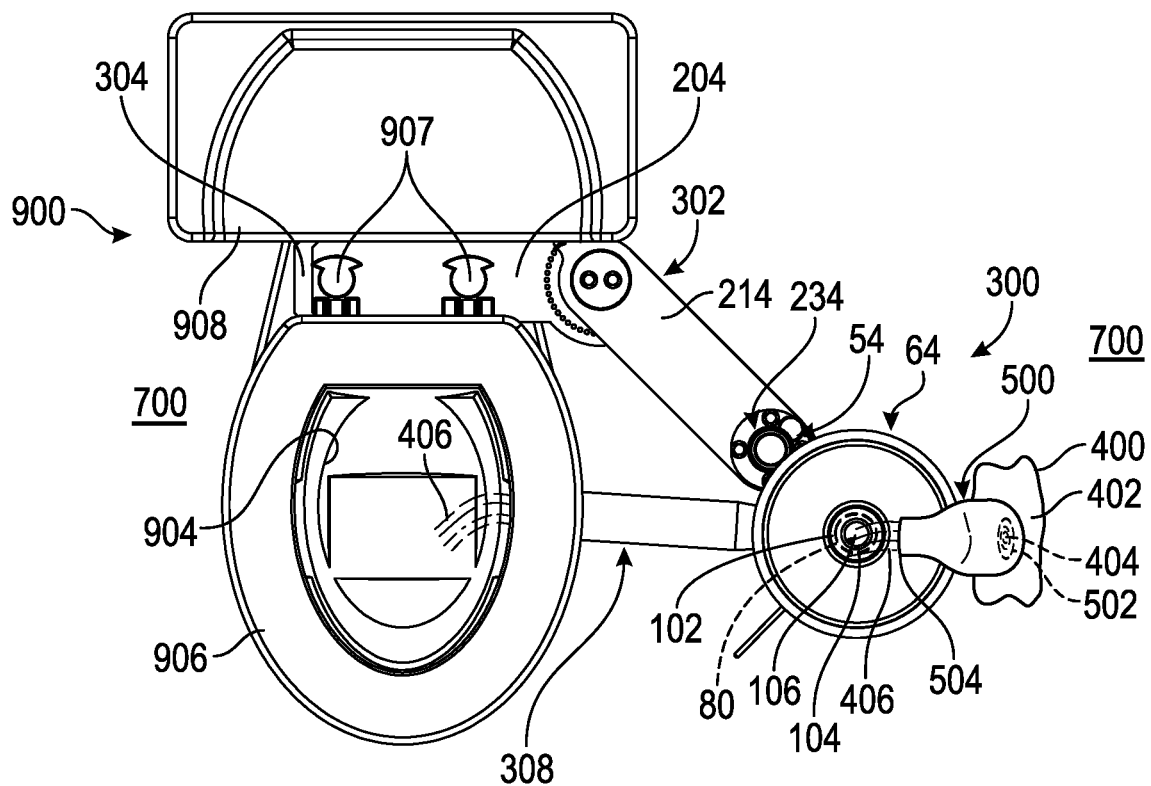
FIG. 17 is a top plan view of the device shown in FIGS. 14-16, further illustrating the device mounted on the toilet shown in FIG. 16 and at least the lower drain portion of the drain positioned over the toilet bowl rim of the toilet beneath the lowered toilet seat of the toilet while the device is in use.
Figure 18:
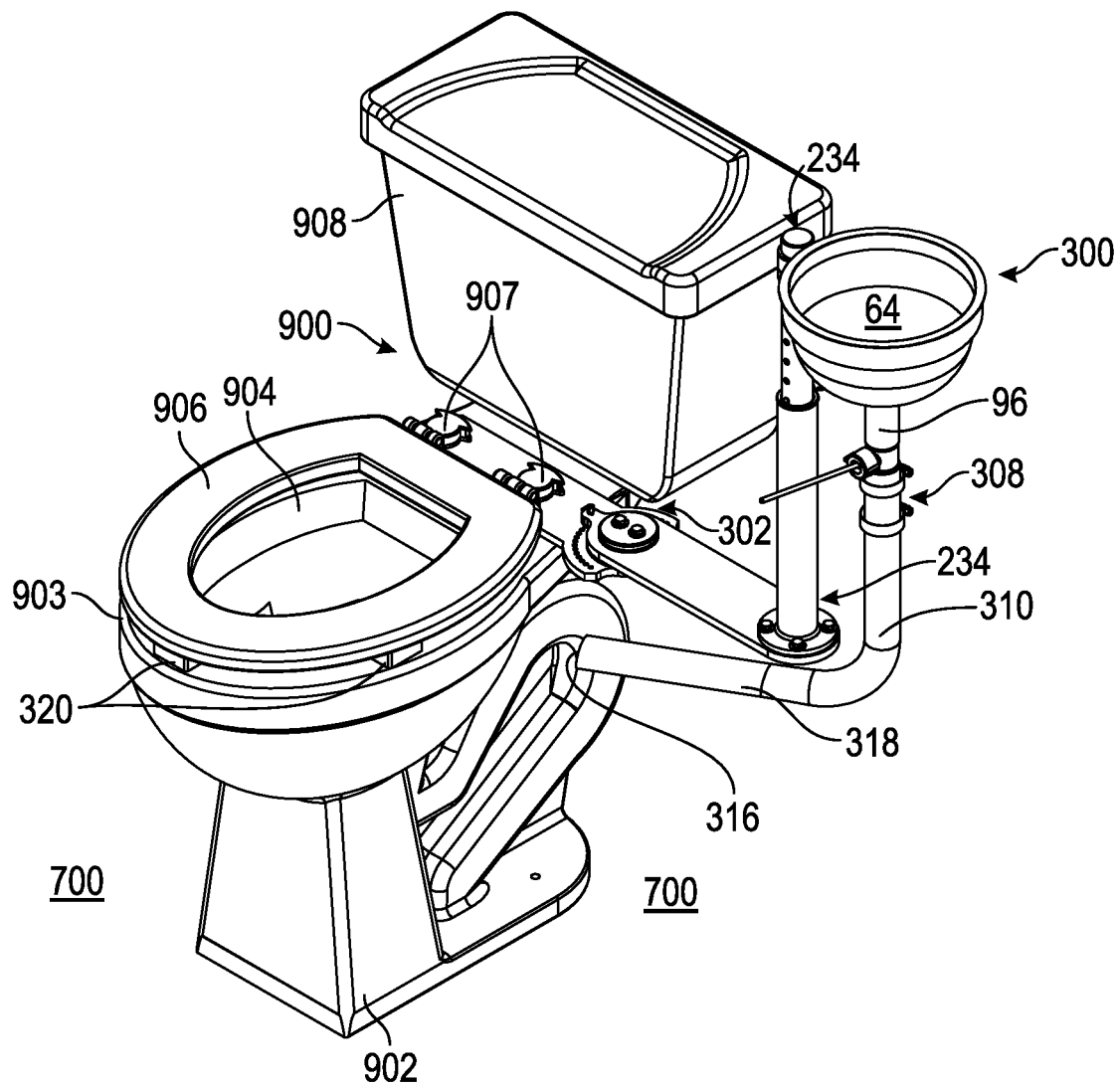
FIG. 18 is a perspective view of the device shown in FIGS. 14-17, illustrating the device mounted on the toilet shown in FIGS. 16 and 17 and at least the lower drain portion of the drain positioned away from the toilet bowl rim and lowered toilet seat of the toilet while the device is not in use.

The base 302 includes a stationary base-mounting portion 304. As shown in FIG. 15, the stationary base-mounting portion 304 may be substantially flat. The stationary base-mounting portion 304 has a pair of mounting holes 306 formed therein. The pair of mounting holes 306 may be spaced apart from each other at a standard width or distance (e.g., corresponding to a pair of toilet seat mounting holes (not shown) of standardized toilets, such as the toilet 900) such that the stationary base-mounting portion 304 may be mounted on the toilet 900 beneath at least a pair of toilet seat mounting portions 907 of a toilet seat 906 of the toilet 900 by way of fasteners (e.g., bolts secured with nuts (not shown)) disposed within and extending downwardly through at least the pair of toilet seat mounting portions 907, the pair of mounting holes 306, and the pair of toilet seat mounting holes (not shown) of the toilet 900, as may be understood by one skilled in the art. In this regard, as shown in FIGS. 17-19, the stationary base-mounting portion 304 of the base 302 is mounted on a base 902 of the toilet 900 rearward of a toilet bowl opening 904 formed in the base 902 and forward of a tank 908 of the toilet 900.

The base 302 further includes a stationary portion 204. As shown in FIG. 15, the stationary portion 204 may be substantially flat. The stationary portion 204 has a pair of mounting holes 206 formed therein. The pair of mounting holes 206 may be spaced apart from each other at the standard width or distance (i.e., corresponding to at least the pair of mounting holes 306 formed in the stationary base-mounting portion 304 of the base 302) such that the stationary portion 204 may be mounted on the toilet 900 above and on the stationary base-mounting portion 304 and beneath the pair of toilet seat mounting portions 907 of the toilet seat 906 of the toilet 900 by way of the fasteners (e.g., the bolts secured with nuts (not shown)) disposed within and extending downwardly through the pair of toilet seat mounting portions 907, the pair of mounting holes 206, the pair of mounting holes 306 formed in the stationary base-mounting portion 304, and the pair of toilet seat mounting holes (not shown) of the toilet 900, as may be understood by one skilled in the art. In this regard, as shown in FIGS. 17-19, the stationary portion 204 is mounted on the toilet 900 such that the stationary portion 204 is mounted above and on the stationary base-mounting portion 304, rearward of the toilet bowl opening 904 formed in the base 902 of the toilet 900, and forward of the tank 908 of the toilet 900. As further shown in FIG. 15, the stationary portion 204 further includes a pivot 208 protruding upwardly from the stationary portion 204. The pivot 208 may be substantially cylindrical and has a plurality of threaded fastener-receiving holes 210 formed therein, as will be further discussed herein. Additionally, the stationary portion 204 further has a plurality of arcuately-aligned holes 212 formed therein, as will be further discussed herein. As further shown in FIG. 15, the plurality of arcuately-aligned holes 212 are disposed adjacent to the pivot 208 of the stationary portion 204.

The base 302 further includes an arm portion 214. As shown in FIG. 15, the arm portion 214 may be substantially flat. As will be further discussed herein, the arm portion 214 has a pivot-receiving opening 216 formed therein (e.g., which may be circular), a threaded locking element-receiving hole 218 formed therein, and a plurality of threaded fastener-receiving holes 220 formed therein.

Figure 14:
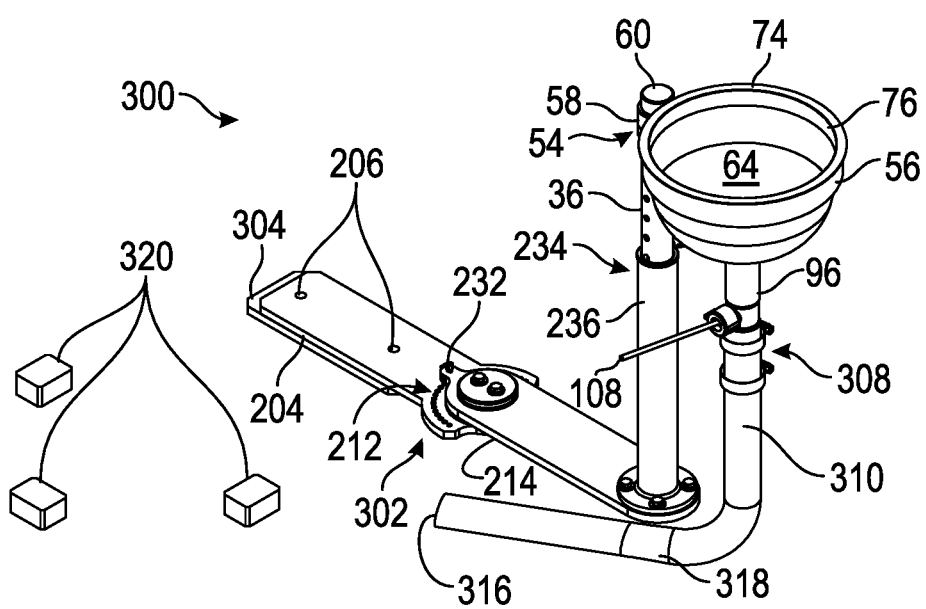
FIG. 14 is a perspective view of yet another illustrative embodiment of a device for sanitarily draining human waste from an ostomy pouch into a toilet.
Figure 19:
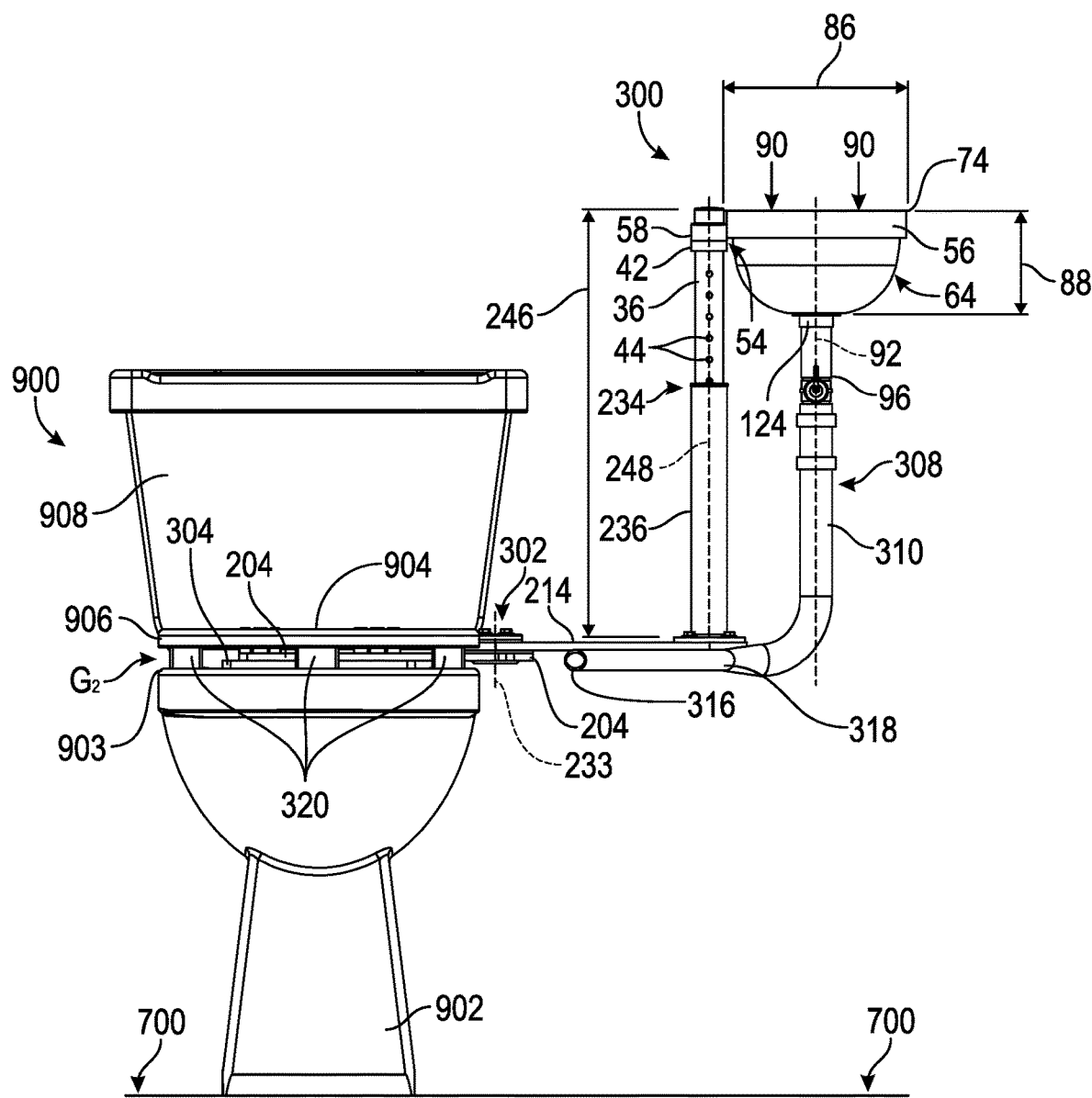
FIG. 19 is a front elevational view of the device shown in FIGS. 14-18, further illustrating the device mounted on the toilet shown in FIGS. 16-18 and at least the lower drain portion of the drain positioned away from the toilet bowl rim and lowered toilet seat of the toilet while the device is not in use.

As shown in FIGS. 14, 15 and 19, the arm portion 214 of the base 302 is pivotally coupled to the stationary portion 204 of the base 302 so as to extend laterally outwardly from the stationary portion 204. More specifically, as a non-limiting example, the base 302 further includes a cap plate 222 having a plurality of fastener-receiving holes 224 formed therein, an annular lower flat bushing (e.g., made of a low-friction plastic) 226, an annular upper flat bushing (e.g., made of a low-friction plastic) 228, and a plurality of threaded fasteners (e.g., bolts with washers) 230. As shown in FIGS. 14 and 15, the pivot 208 of the stationary portion 204 is disposed within and extends through the pivot-receiving opening 216 formed in the arm portion 214, with the annular lower flat bushing 226 disposed around the pivot 208 beneath the arm portion 214 and with the annular upper flat bushing 228 disposed around the pivot 208 above the arm portion 214. The cap plate 222 is disposed over the annular upper flat bushing 228 and is coupled to the pivot 208 by way of the plurality of threaded fasteners 230 extending through the plurality of fastener-receiving holes 224 formed in the cap plate 222 and being secured within the plurality of threaded fastener-receiving holes 210 formed in the pivot 208, thereby pivotally coupling the arm portion 214 of the base 302 to the stationary portion 204 of the base 302. In this regard, as shown in FIG. 19, the arm portion 214 may be pivoted about the pivot 208 of the stationary portion 204 about a vertically-extending pivot axis 233 in a smooth, low-friction manner (i.e., as a result of the annular lower flat bushing 226 being disposed between the stationary portion 204 and the arm portion 214, and the annular upper flat bushing 228 being disposed between the arm portion 214 and the cap plate 222).

As further shown in FIGS. 14-19, and shown in FIGS. 14 and 15, the arm portion 214 of the base 302 may be pivoted and locked into one of a plurality of different positions with respect to the stationary portion 204 of the base 302. More specifically, as a non-limiting example, the base 302 further includes a locking element (e.g., a threaded indexing plunger having an internal spring-loaded pin (not shown) retractable by a knob or other pull) 232 secured within the threaded locking element-receiving hole 218 formed in the arm portion 214 such that the internal spring-loaded pin thereof extends into one of the plurality of arcuately-aligned holes 212 formed in the stationary portion 204. As will be further discussed herein, the locking element 232 may be pulled and held such that the internal spring-loaded pin thereof is retracted from one of the plurality of arcuately-aligned holes 212 formed in the stationary portion 204. The arm portion 214 may then be pivoted about the pivot 208 of the stationary portion 204 (i.e., about the vertically-extending pivot axis 233) until the arm portion 214 is in a desired position (i.e., corresponding to one of the plurality of arcuately-aligned holes 212) with respect to the stationary portion 204. Once the arm portion 214 is in the desired position, the locking element 232 may be released and lowered such that the internal spring-loaded pin thereof extends into one of the plurality of arcuately-aligned holes 212, thereby locking the arm portion 214 of the base 302 into the desired position with respect to the stationary portion 204 of the base 302.

Regarding overall construction of the base 302, the stationary portion 204 and the arm portion 214 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 14-19, the device 300 further includes a main support 234. The main support 234 includes a lower support portion 236 having a lower end 238 and an upper end 242. As a non-limiting example, the lower support portion 236 may be elongated, substantially tubular, and may be circular in cross-section. Moreover, the lower support portion 236 may be rigid and non-bendable so as to advantageously provide stability to the device 300 while in use. As shown in FIG. 15, the lower end 238 of the lower support portion 236 is in the form of a flange having a plurality of fastener-receiving holes 240 formed therein. In this regard, the lower support portion 236 is coupled to the base 302 so as to extend upwardly from the base 302. More specifically, the lower end 238 of the lower support portion 236 is coupled to the arm portion 214 of the base 302 by way of a plurality of threaded fasteners (e.g., bolts with washers) 244 extending through the plurality of fastener-receiving holes 240 formed in the lower end 238 and being secured within the plurality of threaded fastener-receiving holes 220 formed in the arm portion 214. As further shown in FIG. 15, a bushing (e.g., a plastic low-friction bushing) 34 is seated within the lower support portion 236 at the upper end 242 thereof, as will be further discussed herein.

The main support 234 further includes an upper support portion 36 having a lower end 38 and an upper end 40. As a non-limiting example, the upper support portion 36 may be elongated, substantially tubular, and may be circular in cross-section. Moreover, the upper support portion 36 may be rigid and non-bendable so as to advantageously provide stability to the device 300 while in use. As will be further discussed herein, as shown in FIG. 15, the upper support portion 36 includes a shoulder 42 coupled thereto proximate the upper end 40 so as to circumscribe or otherwise surround an exterior of the upper support portion 36. Additionally, the upper support portion 36 has a plurality of vertically-aligned side holes 44 formed therein. The upper support portion 36 extends through the bushing 34 and is at least partially disposed within the lower support portion 236 such that the upper support portion 36 is slidably engaged (e.g., telescopically) with the lower support portion 236. In this regard, a removable fastener (e.g., a pin) 46 is inserted into one of the vertically-aligned side holes 44 such that an overall vertical height 246 of the main support 234 may be adjusted along a vertically-extending center axis 248 of the main support 234. Moreover, as shown in FIGS. 14 and 15, an outwardly-protruding portion 48 of the removable fastener 46 may be supported on the upper end 242 of the lower support portion 236 once the removable fastener 46 is inserted into one of the vertically-aligned side holes 44 to maintain the adjusted overall vertical height 246 of the main support 234. In this regard, the upper support portion 36 may be advantageously grasped and lifted to slide upwardly or pivot with respect to the lower support portion 236, or may be removed from the lower support portion 236 entirely, without the need to remove the removable fastener 46 from the upper support portion 36.

Regarding overall construction of the main support 234, the lower support portion 236 and the upper support portion 36 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 14-19, the device 300 further includes a holder 54. As shown in FIG. 15, the holder 54 includes a holding portion 56 and a coupling portion 58 fixed to the holding portion 56. As a non-limiting example, the holding portion 56 and the coupling portion 58 may each be ring-shaped and may abut each other in a fixed, side-by-side manner. Additionally, as shown in FIG. 19, part of the coupling portion 58 may be disposed lower than the holding portion 56. Moreover, the ring-shape of the holding portion 56 may be substantially larger in diameter than the ring-shape of the coupling portion 58. The holding portion 56 and the coupling portion 58 may be formed as separate pieces before being fixed to each other, or may be monolithically formed together as a single piece, as may be understood by one skilled in the art.

As shown in FIGS. 14, 18 and 19, the holder 54 is pivotally coupled to the main support 234. More specifically, the coupling portion 58 of the holder 54 is pivotally coupled to the upper support portion 36 of the main support 234 proximate the upper end 40 of the upper support portion 36. In this regard, at least part of the upper support portion 36 extends through the coupling portion 58 such that the coupling portion 58 is pivotally supported on the shoulder 42 of the upper support portion 36 so as to circumscribe or otherwise surround the exterior of the upper support portion 36. As shown in FIG. 15, a cap 60 and a washer 62 are coupled at or proximate the upper end 40 of the upper support portion 36 of the main support 234, above and proximate the coupling portion 58 of the holder 54, such that the coupling portion 58 is stably maintained on the shoulder 42 of the upper support portion 36 while pivotally coupled to the upper support portion 36. In this regard, as will be further discussed herein, with the coupling portion 58 of the holder 54 pivotally coupled to the main support 234, the holding portion 56 of the holder 54 is disposed laterally outboard of the coupling portion 58 and the entire holder 54 may be pivoted about the vertically-extending center axis 248 of the main support 234.

Regarding overall construction of the holder 54, the holding portion 56 and the coupling portion 58 thereof may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

Figure 16:
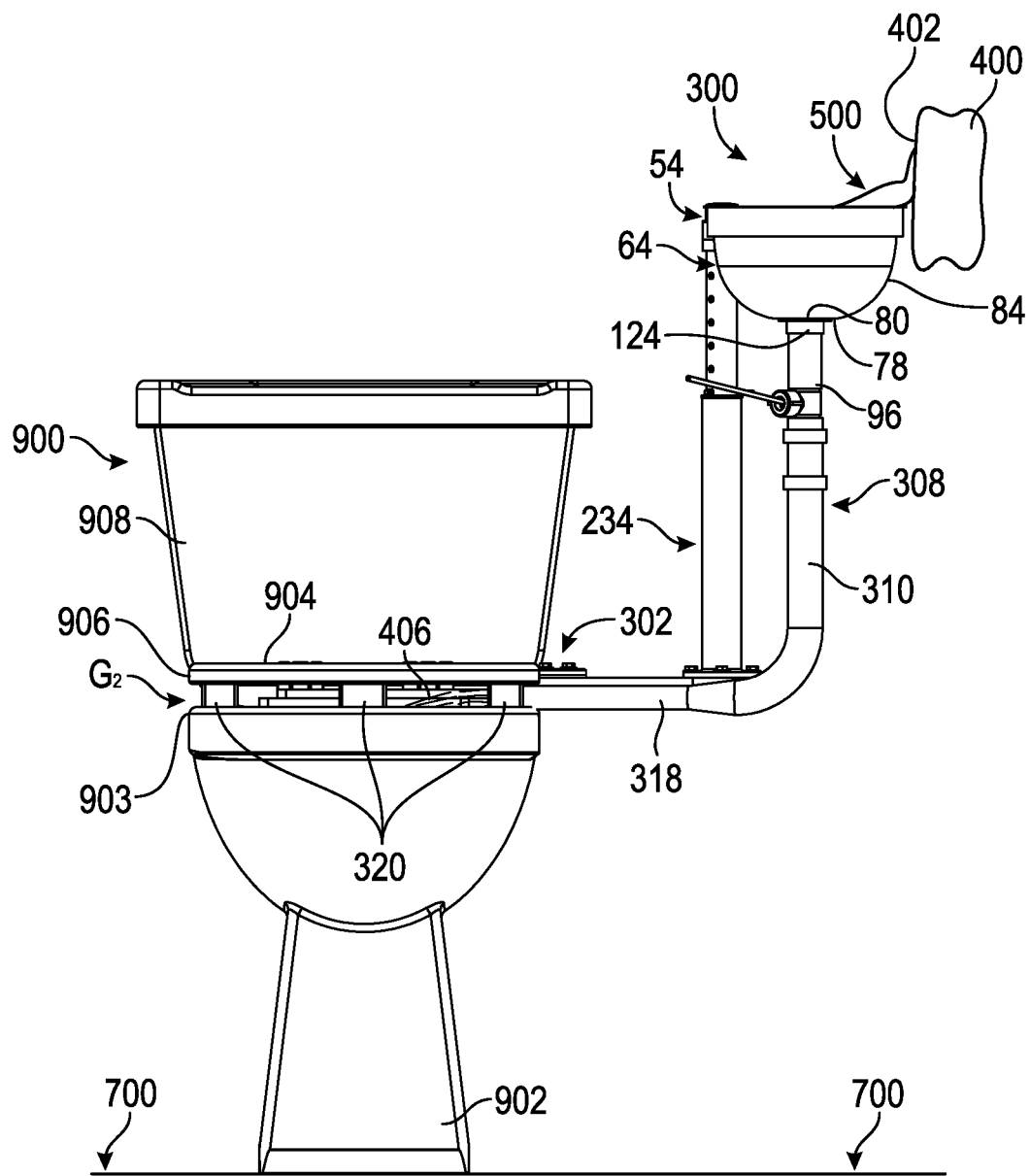
FIG. 16 is a front elevational view of the device shown in FIGS. 14 and 15, illustrating the device mounted on a toilet and at least a lower drain portion of a drain of the device positioned over a toilet bowl rim of the toilet beneath a lowered toilet seat of the toilet while the device is in use.

As further shown in FIGS. 14-19, the device 300 further includes a basin 64. As shown in FIGS. 15, 16 and 19, the basin 64 has an upper portion 66, a lower portion 68, and an intermediate portion 70 disposed between the upper portion 66 and the lower portion 68. The upper portion 66 of the basin 64 has a top end 72 having a top lip (e.g., an annular edge) 74 forming a top opening 76 therein, and the lower portion 68 of the basin 64 has a bottom end 78 having a bottom opening 80 formed therein. As a non-limiting example, the basin 64 may be bowl-shaped, which may be particularly advantageous as will be further discussed herein. In this regard, the basin 64 may have a generally concave inner surface 82 extending from the top end 72 to the bottom end 78 and entirely around the basin 64, and an opposing generally convex outer surface 84 extending from the top end 72 to the bottom end 78 and entirely around the basin 64. Additionally, the top lip 74 may be ring-shaped, may be oriented substantially horizontally, and may extend entirely around the top end 72 of the basin 64. Moreover, an overall lateral width (i.e., diameter) 86 of the basin 64 may be greater than an overall vertical height (i.e., depth) 88 of the basin 64, which may be particularly advantageous as will be further discussed herein.

As shown in FIGS. 14 and 16-19, the basin 64 is retained by the holder 54 such that the basin 64 is operably coupled to the main support 234 by way of the holder 54. More specifically, the basin 64 is inserted into the holding portion 56 of the holder 54 such that at least part of the upper portion 66 of the basin 64 is seated or otherwise disposed within the holding portion 56 and the top lip 74 of the basin 64 engages the holding portion 56. In this regard, the top lip 74 of the basin 64 is supported by the holding portion 56 of the holder 54 such that at least the weight 90 of the basin 64 is applied to the holder 54 by way of at least the top lip 74, thereby advantageously stably maintaining the basin 64 within the holding portion 56 while being retained by the holder 54, yet advantageously allowing the basin 64 to be quickly and easily lifted and removed entirely from the holder 54 as desired while the holder 54 remains pivotally coupled to the main support 234. Additionally, as further shown in FIGS. 14 and 16-19, since the upper portion 66 of the basin 64 is at least partially circumscribed or otherwise surrounded by the holding portion 56 of the holder 54 at a location above the lower portion 68 of the basin 64, the basin 64 advantageously maintains a stabilizing lower center of gravity within the holding portion 56 while being retained by the holder 54. Moreover, as will be further discussed herein, with the basin 64 retained by the holding portion 56 of the holder 54, a vertically-extending center axis 92 of the basin 64 is laterally offset from, and parallel to, the vertically-extending pivot axis 233 of the base 302 and the vertically-extending center axis 248 of the main support 234. In this regard, as shown in FIG. 19, the basin 64, together with the holder 54, may be pivoted about the vertically-extending center axis 248 of the main support 234. Moreover, as further shown in FIG. 19, the basin 64, together with the holder 54 and the main support 234, may be pivoted about the vertically-extending pivot axis 233 of the base 302 when the arm portion 214 of the base 302 is pivoted with respect to the stationary portion 204 of the base 302.

While not shown, in an alternative configuration, the holder 54 includes the coupling portion 58 without the holding portion 56, and the coupling portion 58 is fixed directly to the basin 64 (e.g., to the upper portion 66 of the basin 64 in a fixed, side-by-side manner) such that the coupling portion 58 of the holder 54 operably couples the basin 64 to the main support 234, as may be understood by one skilled in the art.

Regarding overall construction of the basin 64, the basin 64 may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

As further shown in FIGS. 14-19, the device 300 further includes a drain 308. As shown in FIG. 15, the drain 308 includes an upper drain portion 96. As a non-limiting example, the upper drain portion 96 may be generally elongated, substantially tubular, and may be circular in cross-section. Additionally, the upper drain portion 96 has an upper end 98 and a lower end 100. The upper end 98 has a flange 102 forming a drain inlet 104 therein. Moreover, as shown in FIG. 17, the upper drain portion 96 includes a valve 106 disposed at least partially therein. The valve 106 is operably coupled to a pivot rod 108 extending generally laterally outwardly from the upper drain portion 96. As will be further discussed herein, the valve 106 may be opened or closed by lowering or lifting the pivot rod 108, as may be understood by one skilled in the art.

While not shown, in an alternative configuration, the valve 106 may be replaced with a pop-up stopper (not shown) which is operably coupled to the pivot rod 108. The pop-up stopper is disposed at least partially within the upper drain portion 96 of the drain 308 and protrudes upwardly above the flange 102 such that the pop-up stopper may be opened (i.e., in an upward position above the flange 102, thereby allowing the drain inlet 104 to remain open) or closed (i.e., in a downward position sealed against the flange 102, thereby closing the drain inlet 104) by lowering or lifting the pivot rod 108, as may be understood by one skilled in the art.

The drain 308 further includes a lower drain portion 310. As a non-limiting example, the lower drain portion 310 may be generally elongated, curved, and substantially tubular. Additionally, the lower drain portion 310 has an upper end 312 and a lower end 314. The upper end 312 may be circular in cross-section and the lower end 314 may be oval-shaped in cross-section, as will be further discussed herein. The lower end 314 of the lower drain portion 310 has a drain outlet 316 formed therein. Additionally, as will be further discussed herein, a lower part 318 of the lower drain portion 310 is elongated, oriented substantially horizontally, and terminates at the lower end 314 of the lower drain portion 310. Moreover, as shown in FIG. 19, the lower part 318 of the lower drain portion 310 may be oval-shaped in cross-section such that the drain outlet 316 formed in the lower end 314 may also be oval-shaped in cross-section, as will be further discussed herein. In this regard, another primary difference between the device 300 and the devices 10, 200 is that the lower drain portion 310 may be curved and shaped differently (e.g., as shown in FIGS. 14-19) than the lower drain portion 110 of the device 10 and the lower drain portion 252 of the device 200.

As shown in FIGS. 14, 16, 18 and 19, the lower drain portion 310 of the drain 308 is removably coupled to the upper drain portion 96 of the drain 308, by way of a plurality of band clamps (e.g., hose clamps) 122, which may be particularly advantageous as will be further discussed herein. In this regard, the lower drain portion 310 is removably coupled to the upper drain portion 96 in a sealed, water-tight manner such that the lower drain portion 310 is in fluid communication with the upper drain portion 96. Moreover, since each device 10, 200, 300 may include the same upper drain portion 96, 96, 96 (i.e., as previously described herein for each device 10, 200, 300) and the respective lower drain portions 110, 252, 310 of each device 10, 200, 300 are each removably coupled to the respective upper drain portions 96, 96, 96 of each device 10, 200, 300, the lower drain portions 110, 252, 310 may therefore be advantageously interchangeable on each device 10, 200, 300, as may be understood by one skilled in the art.

As shown in FIGS. 16, 17 and 19, the drain 308 is coupled to the basin 64 at the bottom opening 80 of the basin 64 such that the drain 308 is in fluid communication with the basin 64. In this regard, the flange 102 of the upper drain portion 96 of the drain 308 is coupled to the bottom end 78 of the basin 64 at the bottom opening 80 of the basin 64 in a sealed, water-tight manner. More specifically, a sealant or gasket (not shown) is disposed between the flange 102 and the bottom end 78 of the basin 64 and a threaded nut 124 (e.g., as shown in FIGS. 16 and 19) is tightened on threads (not shown) of the upper drain portion 96, below and against the bottom end 78 of the basin 64, such that the flange 102 is coupled (i.e., in the sealed, water-tight manner) to the bottom end 78 of the basin 64 and the drain inlet 104 of the upper drain portion 96 is disposed at the bottom opening 80 of the basin 64. As shown in FIGS. 14, 16, 18 and 19, with the drain 308 coupled to basin 64 and with the basin 64 retained by the holder 54, the basin 64 and the drain 308, together with the holder 54, may be pivoted about the vertically-extending center axis 248 of the main support 234. Additionally, as further shown in FIGS. 14, 16, 18 and 19, with the drain 308 coupled to basin 64 and with the basin 64 retained by the holder 54, the basin 64 and the drain 308, together with the holder 54 and the main support 234, may be pivoted about the vertically-extending pivot axis 233 of the base 302 when the arm portion 214 of the base 302 is pivoted with respect to the stationary portion 204 of the base 302. Moreover, with the drain 308 coupled to the basin 64 and with the basin 64 retained by the holder 54, the basin 64 and the drain 308 together may be quickly and easily lifted and removed entirely from the holder 54 (e.g., with the drain 308 being lifted upwardly through the holding portion 56 of the holder 54) as desired while the holder 54 remains pivotally coupled to the main support 234. In this regard, once the basin 64 has been lifted upwardly and removed entirely from the holder 54, the basin 64 may be further lifted and tilted at various angles such that the drain 308 may be lifted upwardly through, and removed entirely from, the holding portion 56 of the holder 54, which may be particularly advantageous as will be further discussed herein.

Regarding overall construction of the drain 308, the upper drain portion 96 thereof may be made of any suitable material (e.g., stainless steel, brass, aluminum, fiber reinforced plastic, etc.) by way of any suitable manufacturing process (e.g., casting, stamping, extrusion, machining, welding, injection molding, etc.), as may be understood by one skilled in the art. Moreover, the lower drain portion 310 of the drain 308 may be made of any suitable material (e.g., rigid or flexible plastic, rubber, etc.) by way of any suitable manufacturing process (e.g., extrusion, injection molding, etc.), as may be understood by one skilled in the art.

As shown in FIGS. 14-16, 18 and 19, the device 300 further includes a plurality of toilet seat spacers (e.g., in the form of injection-molded plastic blocks) 320. Each of the toilet seat spacers 320 may be thicker (i.e., with regard to vertical height) than each of the toilet seat spacers 262 of the device 200, for reasons that will be understood by one skilled in the art. More specifically, as previously discussed herein, the stationary base-mounting portion 304 and the stationary portion 204 of the base 302 of the device 300 may be mounted on the toilet 900 beneath the pair of toilet seat mounting portions 907 of the toilet seat 906 of the toilet 900. In this regard, as shown in FIGS. 16, 18 and 19, a gap $G_2$ may therefore be defined between the lowered toilet seat 906 and at least a toilet bowl rim 903 (i.e., which surrounds the toilet bowl opening 904) of the base 902 of the toilet 900. Since the base 302 includes the additional stationary base-mounting portion 304 as compared to the base 202 of the device 200, the gap $G_2$ may therefore be larger (i.e., in terms of vertical height) than the gap $G_1$ defined with the device 200 (i.e., shown in FIGS. 10, 12 and 13). In this regard, as will be further discussed herein, it is advantageously intentional that the gap $G_2$ be larger than the gap $G_1$, which is made possible by including the additional stationary base-mounting portion 304 together with the stationary portion 204 of the base 302. Nevertheless, as a result of the gap $G_2$ being defined, the toilet seat 906 could slope downwardly and bend in an unlevel manner when lowered (i.e., possibly causing unwanted stress on the pair of toilet seat mounting portions 907 of the toilet seat 906). In this regard, as further shown in FIGS. 16, 18 and 19, the plurality of toilet seat spacers 320 are secured to the toilet seat 906 or to the toilet bowl rim 903 (e.g., by way of an adhesive or an adhesive tape) such that the toilet seat spacers 320 are disposed within the gap $G_2$ and the toilet seat 906 is advantageously stable and level when lowered without causing possible unwanted stress on the pair of toilet seat mounting portions 907 of the toilet seat 906, as may be understood by one skilled in the art. Moreover, as shown in FIGS. 16 and 17, the larger gap $G_2$ advantageously allows at least the lower part 318 (i.e., which may be oval-shaped in cross-section, as previously discussed herein) of the lower drain portion 310 of the drain 308 to be positioned over the toilet bowl rim 903 of the toilet 900 beneath the lowered toilet seat 906 such that at least the drain outlet 316 formed in the lower end 314 of the lower drain portion 310 is disposed over or proximate the toilet bowl opening 904 of the toilet 900, as will be further discussed herein.

While not shown, in an alternative configuration, the plurality of toilet seat spacers 320 and the toilet seat 906 are monolithically formed together as a single piece (e.g., by way of injection molding), as may be understood by one skilled in the art.

As shown in FIGS. 20 and 21, the device 300 optionally further includes at least one accessory for advantageously providing additional conveniences while using the device 300. As a non-limiting example, the at least one accessory may be at least one or more of a toilet paper holder 126 for holding a roll of toilet paper (not shown), a tissue box holder 130 for holding a tissue box (not shown) and a sprayer holder 134 for holding a sprayer 138 (e.g., which may be connected to a hose (not shown) connected directly or indirectly to a toilet water supply valve (not shown), depending on the number of water connections the toilet water supply valve may have and whether or not an intermediate hose splitter (not shown) is employed). Other accessories may also be included, as may be understood by one skilled in the art.

As further shown in FIGS. 20 and 21, the toilet paper holder 126 includes a coupling portion 128 that engages the holding portion 56 of the holder 54 such that the toilet paper holder 126 is retained by the holder 54 proximate the basin 64 (i.e., adjacent to the upper portion 66 of the basin 64 and at least partially beneath the top lip 74 of the basin 64). Additionally, the tissue box holder 130 includes one or more coupling portions 132 that engage the holding portion 56 of the holder 54 such that the tissue box holder 130 is retained by the holder 54 proximate the basin 64 (i.e., adjacent to the upper portion 66 of the basin 64 and at least partially beneath the top lip 74 of the basin 64). Moreover, the sprayer holder 134 includes a coupling portion 136 that engages the holding portion 56 of the holder 54 such that the sprayer holder 134 is retained by the holder 54 proximate the basin 64 (i.e., adjacent to the upper portion 66 of the basin 64 and at least partially beneath the top lip 74 of the basin 64). In this regard, with any of the toilet paper holder 126, the tissue box holder 130 and the sprayer holder 134 retained by the holding portion 56 of the holder 54, the top lip 74 of the basin 64 advantageously stably maintains any of the toilet paper holder 126, the tissue box holder 130 and the sprayer holder 134 on the holder 54 since at least the weight 90 of the basin 64, and therefore the additional weight of the drain 308 as well, is applied to any of the toilet paper holder 126, the tissue box holder 130 and the sprayer holder 134, and therefore to the holder 54 as well, by way of at least the top lip 74, as previously discussed herein.

Regarding overall construction of the at least one accessory, any of the toilet paper holder 126, the tissue box holder 130 and the sprayer holder 134 may be made of any suitable material (e.g., stainless steel, aluminum, fiber reinforced plastic, etc.) by way of any suitable manufacturing process (e.g., casting, stamping, extrusion, machining, welding, injection molding, etc.), as may be understood by one skilled in the art.

Referring to FIGS. 16-19, overall use of the device 300, including the draining of the human waste 406 from the ostomy pouch 500 into the toilet 900, will now be described in detail. The device 300 is installed on the toilet 900 by way of the base 302 of the device 300 being mounted on the toilet 900 (i.e., in a manner as previously discussed herein).

As shown in FIGS. 16 and 17, with the toilet seat 906 of the toilet 900 lowered, if needed, a person 400 may adjust the overall vertical height 246 of the main support 234 (i.e., in a manner as previously discussed herein) such that at least the lower part 318 of the lower drain portion 310 of the drain 308 is disposed at a same height as the gap $G_2$ (i.e., defined between the lowered toilet seat 906 and at least the toilet bowl rim 903 of the toilet 900). The person 400 may then pull and hold the locking element 232 of the base 302 such that the arm portion 214 of the base 302 may then be unlocked (i.e., in a manner as previously discussed herein) and pivoted about the pivot 208 (i.e., towards the toilet 900 and about the vertically-extending pivot axis 233) of the stationary portion 204 of the base 302. In this regard, the basin 64 and the drain 308, together with the holder 54 and the main support 234, may be pivoted towards the toilet 900 when the arm portion 214 is pivoted with respect to the stationary portion 204 such that at least the lower part 318 of the lower drain portion 310 of the drain 308 is disposed within the gap $G_2$ and positioned over the toilet bowl rim 903 beneath the lowered toilet seat 906. Moreover, with at least the lower part 318 of the lower drain portion 310 disposed within the gap $G_2$ and positioned over the toilet bowl rim 903 beneath the lowered toilet seat 906, at least the drain outlet 316 formed in the lower end 314 of the lower drain portion 310 is disposed over or proximate the toilet bowl opening 904 of the toilet 900. Moreover, the person 400 may then release the locking element 232 of the base 302 such that the arm portion 214 of the base 302 is locked into the desired position (i.e., in a manner as previously discussed herein) with respect to the stationary portion 204 of the base 302. Regarding the person 400, it is to be understood that merely a portion of the person 400, which includes at least part of an abdomen 402 having a stoma 404, is schematically shown. Additionally, the ostomy pouch 500 (i.e., that needs draining) containing the human waste 406 therein is schematically shown. The ostomy pouch 500 is temporarily secured to the abdomen 402 of the person 400 such that an inlet 502 of the ostomy pouch 500, disposed at an attachment end of the ostomy pouch 500, is secured around the stoma 404, thereby allowing the human waste 406 to flow out of the stoma 404 and be collected and temporarily stored within the ostomy pouch 500.

As further shown in FIGS. 16 and 17, to drain the human waste 406 from the ostomy pouch 500 into the toilet 900, the person 400 may stand proximate the basin 64 of the device 300 while the ostomy pouch 500 remains secured to the abdomen 402 of the person 400. In this regard, the person 400 may therefore stand in a relaxed, upright position, thereby advantageously avoiding the need to stand over the toilet 900, sit on the toilet 900, straddle the toilet 900, or kneel on the floor 700 next to the toilet 900. Preferably, the top end 72 of the basin 64 is disposed at a height below at least a portion of the ostomy pouch 500 such that the ostomy pouch 500 slopes generally downwardly when a closure end (i.e., sometimes referred to as a tail) of the ostomy pouch 500 is positioned over the top opening 76 of the basin 64 (i.e., to better facilitate draining the human waste 406 from the ostomy pouch 500).

As further shown in FIGS. 16 and 17, the person 400 may then position the closure end of the ostomy pouch 500 over the top opening 76 of the basin 64 and preferably at least partially within the basin 64. In this regard, since the overall lateral width 86 of the basin 64 may be greater than the overall vertical height 88 of the basin 64 (i.e., as previously discussed herein), the top end 72 of the basin 64, including the top opening 76 of the basin 64, may advantageously provide a relatively wide space (i.e., target area) for the person 400 to drain the ostomy pouch 500, thereby advantageously reducing the likelihood of the human waste 406 spilling or splashing outside of the basin 64. The person 400 may then open the closure end of the ostomy pouch 500 such that an outlet 504 of the ostomy pouch 500 is open. In this regard, the human waste 406 temporarily stored within the ostomy pouch 500 may then freely drain from the ostomy pouch 500 such that the human waste 406 flows out of the outlet 504 of the ostomy pouch 500 and into the basin 64. Moreover, since the basin 64 may be bowl-shaped (i.e., as previously discussed herein), the human waste 406 received within the basin 64 from the ostomy pouch 500 may advantageously flow downwardly within the basin 64 in a relatively efficient, unimpeded manner (i.e., with reduced drag as a result of the bowl-shape of the basin 64), thereby advantageously further reducing the likelihood of the human waste 406 spilling or splashing outside of the basin 64. In this regard, with the valve 106 of the drain 308 open, the human waste 406 received within the basin 64 from the ostomy pouch 500 may flow downwardly into the drain inlet 104 of the drain 308 such that the drain 308 directs and drains any human waste 406 received from the basin 64 into the toilet 900 (i.e., by way of the human waste 406 exiting the drain outlet 316 of the drain 308).

Once the human waste 406 is entirely drained from the ostomy pouch 500, with the valve 106 of the drain 308 open or closed, and with the ostomy pouch 500 still secured to the abdomen 402 of the person 400 or with the ostomy pouch 500 removed from the abdomen 402, the person 400 may advantageously wash or otherwise sanitize the ostomy pouch 500 (e.g., such as with the sprayer 138, as previously discussed herein) within the basin 64 before reattaching (i.e., if removed) the ostomy pouch 500 to the abdomen 402 or reclosing the closure end of the ostomy pouch 500 such that the outlet 504 of the ostomy pouch 500 is closed. In this regard, with the valve 106 of the drain 308 open, any water or other substance used to wash or otherwise sanitize the ostomy pouch 500 is advantageously directed and drained into the toilet 900 by way of the drain 308. Additionally, the person 400 may advantageously wash or otherwise sanitize the device 300, including the basin 64 and the drain 308 (e.g., such as with the sprayer 138, as previously discussed herein), while at least the lower part 318 of the lower drain portion 310 of the drain 308 remains disposed within the gap $G_2$ and positioned over the toilet bowl rim 903 beneath the lowered toilet seat 906. Moreover, as previously discussed herein, if desired, the person 400 may advantageously (i.e., quickly and easily) lift and remove the basin 64 and the drain 308 entirely from the holder 54 while the holder 54 remains pivotally coupled to the main support 234 such that at least the basin 64 and the drain 308 may be washed or otherwise sanitized at a location away from the toilet 900.

As further shown in FIGS. 16 and 17, when the device 300 is not in use, the device 300 may advantageously remain in an in-use position (i.e., shown in FIGS. 16 and 17) with at least the lower part 318 of the lower drain portion 310 of the drain 308 disposed within the gap $G_2$ and positioned over the toilet bowl rim 903 of the toilet 900 beneath the lowered toilet seat 906 of the toilet 900. In this regard, with the device 300 remaining in the in-use position, people that may not require use of the device 300 are still advantageously allowed to gain unobstructed access to the toilet 900 since at least the lower part 318 of the lower drain portion 310 of the drain 308 remains disposed below the lowered toilet seat 906 and primarily laterally outboard of the lowered toilet seat 906.

As shown in FIGS. 18 and 19, when the device 300 is not in use, the person 400 or other person may optionally pull and hold the locking element 232 of the base 302 such that the arm portion 214 of the base 302 may then be unlocked (i.e., in a manner as previously discussed herein) and pivoted (i.e., away from the toilet 900) about the pivot 208 of the stationary portion 204 of the base 302. In this regard, the basin 64 and the drain 308, together with the holder 54 and the main support 234, may be pivoted away from the toilet 900 when the arm portion 214 is pivoted with respect to the stationary portion 204 (i.e., in a manner opposite of the manner previously discussed herein) such that at least the lower drain portion 310 of the drain 308 is positioned away from the toilet bowl rim 903 and lowered toilet seat 906 of the toilet 900, thereby further advantageously allowing people that may not require use of the device 300 to gain unobstructed access to the toilet 900.

While one or more illustrative embodiments are described above, it is not intended that these illustrative embodiments describe all possible forms of the present disclosure. Rather, the words used in the specification are words of description rather than limitation, and it is understood that various changes may be made without departing from the spirit and scope of the present disclosure.

With regard to any processes, systems, methods, heuristics, etc., described herein, it should be understood that, although the steps of such processes, etc., have been described as occurring according to a certain ordered sequence, such processes could be practiced with the described steps performed in an order other than the order described herein. It should be further understood that certain steps could be performed simultaneously, that other steps could be added, or that certain steps described herein could be omitted. In other words, the descriptions of any processes described above are provided for the purpose of illustrating certain embodiments, and should in no way be construed so as to limit the claims.

As used in this specification and claims, the terms "for example"/("e.g."), "for instance", "such as", and "like", and the verbs "comprising", "having", "including", and their other verb forms, when used in conjunction with a listing of one or more carriers or other items, are each to be construed as open-ended, meaning that the listing is not to be considered as excluding other, additional carriers or items. Other terms are to be construed using their broadest reasonable meaning unless they are used in a context that requires a different interpretation.

What is claimed is:

1. A device for sanitarily draining human waste from an ostomy pouch into a toilet, the device comprising:
    a base;
    a main support coupled to the base;
    a holder coupled to the main support;
    a basin retained by the holder, the basin having a vertically-extending center axis, a top end having a top lip forming a top opening, a bottom end having a bottom opening formed therein, an inner surface extending continuously from the top end to the bottom opening and entirely around the vertically-extending center axis, and an outer surface extending continuously from the top end to the bottom opening and entirely around the vertically-extending center axis, the top lip of the basin being supported by the holder such that at least the weight of the basin is applied to the holder by way of at least the top lip; and
    a drain coupled to the basin at the bottom opening of the basin such that the drain is in fluid communication with the basin;
    wherein the basin is capable of receiving therein human waste drained from an ostomy pouch; and
    wherein the drain is capable of at least directing and draining any human waste received from the basin into a toilet.

2. The device according to claim 1, wherein the base is not configured to be mounted on a vertical wall in a room or space in which the toilet is located.

3. The device according to claim 1, wherein the base includes a central portion and a plurality of legs extending laterally outwardly from the central portion, and wherein the main support is coupled to the central portion and extends upwardly from the central portion.

4. The device according to claim 1, wherein the base includes a stationary portion capable of being mounted on the toilet rearward of a toilet bowl opening of the toilet and forward of a tank of the toilet, and an arm portion pivotally coupled to the stationary portion and extending laterally outwardly from the stationary portion, and wherein the main support is coupled to the arm portion and extends upwardly from the arm portion.

5. The device according to claim 4, wherein the arm portion of the base is capable of being pivoted and locked into one of a plurality of different positions with respect to the stationary portion of the base.

6. The device according to claim 1, wherein the main support includes a lower support portion and an upper support portion, the lower support portion being coupled to the base and extending upwardly from the base, the upper support portion being slidably engaged with the lower support portion such that an overall vertical height of the main support is adjustable, and wherein the holder is coupled to the upper support portion.

7. The device according to claim 1, wherein the holder is pivotally coupled to the main support.

8. The device according to claim 1, wherein the holder includes a holding portion and a coupling portion fixed to the holding portion, the coupling portion being coupled to the main support, the holding portion being disposed laterally outboard of the coupling portion, and wherein the basin is retained by the holding portion.

9. The device according to claim 1, wherein the top lip of the basin engages the holder.

10. The device according to claim 1, wherein the drain includes a valve disposed at least partially within the drain.

11. The device according to claim 1, wherein the drain includes an upper drain portion having a drain inlet disposed at the bottom opening of the basin and a lower drain portion having a drain outlet, the lower drain portion being removably coupled to the upper drain portion, and wherein at least a lower part of the lower drain portion is capable of being positioned over a toilet bowl opening of the toilet.

12. The device according to claim 1, wherein the drain includes an upper drain portion having a drain inlet disposed at the bottom opening of the basin and a lower drain portion having a drain outlet, the lower drain portion being removably coupled to the upper drain portion, and wherein at least a lower part of the lower drain portion is oriented substantially horizontally and is capable of being positioned over a toilet bowl rim of the toilet beneath a lowered toilet seat of the toilet.

13. The device according to claim 1, further comprising at least one of a toilet paper holder retained by the holder proximate the basin, a tissue box holder retained by the holder proximate the basin and a sprayer holder retained by the holder proximate the basin.

14. A device for sanitarily draining human waste from an ostomy pouch into a toilet, the device comprising:
    a base;
    a main support coupled to the base;
    a holder coupled to the main support;
    a basin retained by the holder, the basin having an upper portion, a lower portion, and an intermediate portion disposed between the upper and lower portions, the upper portion of the basin having a top end having a top opening formed therein, the lower portion of the basin having a bottom end having a bottom opening formed therein, the basin being at least partially surrounded by the holder at a location above the lower portion of the basin; and
    a drain coupled to the basin at the bottom opening of the basin such that the drain is in fluid communication with the basin;

wherein the basin is capable of being lifted and removed from the holder while the holder is coupled to the main support;

wherein the basin is further capable of receiving therein human waste drained from an ostomy pouch; and wherein the drain is capable of at least directing and draining any human waste received from the basin into a toilet.

15. The device according to claim 14, wherein the base is not configured to be mounted on a vertical wall in a room or space in which the toilet is located.

16. The device according to claim 14, wherein the top end of the basin further has a top lip forming the top opening of the basin, and wherein the top lip of the basin is supported by the holder such that at least the weight of the basin is applied to the holder by way of at least the top lip.

17. A device for sanitarily draining human waste from an ostomy pouch into a toilet, the device comprising:

a base;

a main support coupled to the base and extending upwardly from the base, the main support having a vertically-extending center axis;

a basin operably coupled to the main support, the basin having a vertically-extending center axis, a top end having a top annular edge forming a top opening, a bottom end having a bottom opening formed therein, a generally concave inner surface extending from the top end to the bottom opening and entirely around the vertically-extending center axis of the basin, and a generally convex outer surface extending from the top end to the bottom opening and entirely around the vertically-extending center axis of the basin, the vertically-extending center axis of the basin being laterally offset from the vertically-extending center axis of the main support; and a drain coupled to the basin at the bottom opening of the basin such that the drain is in fluid communication with the basin;

wherein the basin is capable of receiving therein human waste drained from an ostomy pouch; and wherein the drain is capable of at least directing and draining any human waste received from the basin into a toilet.

18. The device according to claim 17, wherein the base is not configured to be mounted on a vertical wall in a room or space in which the toilet is located.

19. The device according to claim 17, wherein the top annular edge of the basin is oriented substantially horizontally and extends entirely around the vertically-extending center axis of the basin, and wherein the top opening and the bottom opening of the basin are coaxial with respect to the vertically-extending center axis of the basin.

20. The device according to claim 17, wherein an overall lateral width of the basin is greater than an overall vertical height of the basin.

21. A device for sanitarily draining human waste from an ostomy pouch into a toilet, the device comprising:

a base including a stationary portion capable of being mounted on a toilet rearward of a toilet bowl opening of the toilet and forward of a tank of the toilet, and an arm portion pivotally coupled to the stationary portion and extending laterally outwardly from the stationary portion;

a main support coupled to the arm portion of the base and extending upwardly from the arm portion, the main support having a vertically-extending center axis;

a holder coupled to the main support;

a basin operably coupled to the main support by way of at least a portion of the holder, the basin having a vertically-extending center axis, a top end having a top opening formed therein, a bottom end having a bottom opening formed therein, an inner surface extending continuously from the top end to the bottom opening and entirely around the vertically-extending center axis of the basin, and an outer surface extending continuously from the top end to the bottom opening and entirely around the vertically-extending center axis of the basin, the vertically-extending center axis of the basin being laterally offset from the vertically-extending center axis of the main support; and a drain coupled to the basin at the bottom opening of the basin such that the drain is in fluid communication with the basin;

wherein the basin is capable of receiving therein human waste drained from an ostomy pouch; and wherein the drain is capable of at least directing and draining any human waste received from the basin into the toilet.

\* \* \* \* \*